US 6,537,320 B1

(12) United States Patent
Michelson

(10) Patent No.: US 6,537,320 B1
(45) Date of Patent: Mar. 25, 2003

(54) SELF-BROACHING, ROTATABLE, PUSH-IN INTERBODY SPINAL FUSION IMPLANT AND METHOD FOR DEPLOYMENT THEREOF

(76) Inventor: Gary K. Michelson, 438 Sherman Canal, Venice, CA (US) 90291

( * ) Notice: Subject to any disclaimer, the term of this patent is extended or adjusted under 35 U.S.C. 154(b) by 0 days.

(21) Appl. No.: 09/429,628

(22) Filed: Oct. 29, 1999

Related U.S. Application Data

(60) Provisional application No. 60/106,216, filed on Oct. 30, 1998.

(51) Int. Cl.[7] ................................................ A61F 2/44
(52) U.S. Cl. ................................................ 623/17.11
(58) Field of Search ........................ 623/17.11–17.16

(56) References Cited

U.S. PATENT DOCUMENTS

| 4,834,757 A | | 5/1989 | Brantigan | |
|---|---|---|---|---|
| 5,015,247 A | | 5/1991 | Michelson | |
| 5,306,309 A | | 4/1994 | Wagner et al. | |
| 5,443,514 A | | 8/1995 | Steffee | |
| 5,489,307 A | * | 2/1996 | Kuslich et al. | 623/17.11 |
| 5,489,308 A | * | 2/1996 | Kuslich et al. | 623/17.11 |
| 5,653,762 A | | 8/1997 | Pisharodi | |
| 5,716,415 A | | 2/1998 | Steffee | |
| 5,766,252 A | | 6/1998 | Henry et al. | |
| 5,776,199 A | | 7/1998 | Michelson | |
| 5,782,919 A | | 7/1998 | Zdeblick et al. | |
| 5,865,845 A | * | 2/1999 | Thalgott | 623/17.11 |
| 5,876,457 A | * | 3/1999 | Picha et al. | 623/17.11 |
| 5,888,224 A | | 3/1999 | Beckers et al. | |
| 5,984,967 A | * | 11/1999 | Zdeblick et al. | 623/17.11 |
| 6,071,310 A | * | 6/2000 | Picha et al. | 623/17.11 |
| 6,117,174 A | * | 9/2000 | Nolan | 623/17.11 |
| 6,143,033 A | * | 11/2000 | Paul et al. | 623/17.11 |
| 6,224,631 B1 | * | 5/2001 | Kohrs | 623/17.11 |
| 6,241,770 B1 | * | 6/2001 | Michelson | 623/17.11 |
| 6,241,771 B1 | * | 6/2001 | Gresser et al. | 623/17.16 |
| 6,258,125 B1 | * | 7/2001 | Paul et al. | 623/17.11 |
| 6,290,724 B1 | | 9/2001 | Marino | |

FOREIGN PATENT DOCUMENTS

| RU | 1107854 | 8/1984 |
|---|---|---|
| WO | WO 95/08306 | 3/1995 |

OTHER PUBLICATIONS

PCT International Search Report dated Apr. 13, 2000 from corresponding application No. PCT/US99/25292.

* cited by examiner

Primary Examiner—David H. Willse
Assistant Examiner—Suzette Jackson
(74) Attorney, Agent, or Firm—Martin & Ferraro, LI

(57) ABSTRACT

An interbody spinal fusion implant for insertion across a disc space between adjacent vertebral bodies of a human spine has a body two top side and two bottom side junctions, with at least a pair of diagonally opposed junctions having a distance therebetween that does not significantly exceed the implant body height. The implant also includes one or more bone penetrating protrusions extending outwardly from at least the upper and lower walls of the implant. The implant is inserted on its side between adjacent vertebral bodies and then rotated 90 degrees into place. The protrusions penetrate the endplates upon rotation, thereby securing the implant within the spine. The implant has at least one passage therethrough from the upper wall to the lower wall to promote fusion through the implant. Because of the specialized opposed junctions overdistraction between the adjacent vertebral bodies is avoided when the implant is rotated from an initial insertion position to a final deployed position. In one suggested implant set, two implants are rotated in opposite directions into their respective final deployed positions, and a third specialized implant is positioned therebetween to lock the three implants together along cooperating surfaces. A method for deploying the push-in implants is also disclosed.

105 Claims, 30 Drawing Sheets

SELF-BROACHING, ROTATABLE, PUSH-IN INTERBODY SPINAL FUSION IMPLANT AND METHOD FOR DEPLOYMENT THEREOF

RELATED APPLICATIONS

This application is a regular application claiming priority to U.S. provisional application Ser. No. 60/106,216 filed Oct. 30, 1998, which is incorporated herein by reference.

BACKGROUND OF THE INVENTION

1. Field of the Invention

The present invention relates generally to improved interbody spinal fusion implants for the immobilization of adjacent vertebral bodies and to a method for deployment thereof. In particular, the invention relates to interbody spinal fusion implants and methods for deployment thereof that significantly preserve the structural support of the dense endplate and subchondral bone regions of the adjacent vertebral bodies while also penetrating those endplates so as to access the vascular subchondral bone of those vertebral bodies for the purpose of achieving interbody spinal fusion at least in part through the implants themselves.

2. Description of the Prior Art

Surgical interbody spinal fusion refers to the method of achieving a bridge of bone tissue in continuity between adjacent vertebral bodies and across the disc space to thereby substantially eliminate relative motion between these adjacent vertebral bodies. The term "disc space" refers to the space between adjacent vertebral bodies normally occupied by a spinal disc. The spinal disc that normally resides between the adjacent vertebral bodies maintains the spacing between those vertebral bodies and, in a healthy spine, allows for the normal relative motion between the vertebral bodies.

Numerous implants to facilitate fusion have been described by Cloward, Brantigan, Michelson, and others, and are known to those skilled in the art. Such fusions have also been achieved with the use of bone grafts placed between the vertebral bodies, such as taught and practiced by Dr. Cloward. Generally, cylindrical implants, which may be threaded, offer the advantage of conforming to an easily prepared recipient bore spanning the disc space and penetrating into each of the adjacent vertebral bodies. Such a bore may be created by use of a drill. Drilling of the bore, however, removes a portion of the endplates and of the subchondral bone.

Human vertebral bodies have a hard outer shell of compacted, dense cancellous bone (sometimes referred to as the cortex) and a relatively softer, inner mass of cancellous bone. Just below the cortex adjacent the disc is a region of bone referred to herein as the "subchondral zone". The outer shell of compact bone (the boney endplate) adjacent to the spinal disc and the underlying subchondral zone are together herein referred to as the boney "end plate region" and, for the purposes of this application, is hereby so defined to avoid ambiguity. The endplate region constitutes the densest bone available to support the fusion implant over its length, and removal of this endplate region by the practice of creating a bore into the vertebral bodies results in the implant coming to rest on the softer and less dense cancellous bone that lies beneath the endplate deeper within the vertebral body.

Other spinal fusion implants are known that incorporate a modified cylindrical or a tapered cylindrical shape that also require the use of a drill to create a bore across the disc space and also result in the removal of a portion of the endplate. Inasmuch as the upper and lower vertebral bodies - contacting surfaces of these types of implants are arc-shaped, absent arching the recipient bed in the vertebral body by drilling, it would not be possible to gain the contact between the vertebral bodies and implant needed to achieve fusion. Such arching of the vertebral bodies to receive the implant results in the removal of the endplate.

Non-cylindrical implants that are pushed into the disc space after a discectomy are also known in the art. While these push-in implants do have the advantage of supporting the adjacent vertebral bodies by contacting a substantial portion of the vertebral endplates, they do not offer the advantages associated with threaded cylindrical implants that are screwed into a bore in the adjacent vertebral bodies to more securely hold these implants in their final fully seated positions. Further, unless the endplate is at least partially decorticated, i.e. worked upon to access the vascularity deep to the outer most aspect of the endplate itself, fusion will not occur.

Non-cylindrical spinal fusion implants that are inserted between the endplates of adjacent vertebral bodies and then rotated 90 degrees into place are also known. However, their cross-sectional configuration causes either unwanted over-distraction of the vertebral bodies as they are rotated or under-distraction between the adjacent vertebral bodies once rotated. For example, an implant having an approximately square or rectangular cross-section when rotated in either a clockwise or counterclockwise direction will result in a maximum distraction of the disc space when the diagonal of the implant is at a right angle (90 degrees) to the adjacent vertebral endplates. This amount of distraction is greater than that achieved by the implant when either of its opposed sides are in contact with the adjacent vertebral bodies. If the space between the adjacent vertebral bodies is too small or the amount of attempted distraction too great, rotation of the implant will either not be possible or the vertebral bodies will be broken. If the space between the adjacent vertebral bodies is sufficiently large to permit rotation of such an implant, then when the implant is rotated to its final position with its opposed sides in contact with the adjacent vertebral bodies, insufficient distraction will be achieved between the vertebral bodies as the opposed sides will have a lesser height between them than the diagonal which rotated through that same space. It should be noted that distraction within the elastic range of deformation is highly desirable because it secures the implant, allows the implant to stabilize the adjacent vertebral bodies relative to each other, and provides the most space for the neural elements both passing through and exiting through those vertebral segments.

Therefore, there exists a need for a spinal fusion implant that permits the endplate region of the adjacent vertebral bodies to be substantially preserved while nevertheless accessing the underlying bone vascularity and which implant can be rotated 90 degrees within the disc space to achieve the optimal distraction in the range of elastic deformation and short of plastic deformation and tissue failure.

SUMMARY OF THE INVENTION

The present invention is an interbody spinal fusion implant allowing for the growth of bone from vertebral body to vertebral body through the implant. The present implant is designed to be pressed into a disc space in which the adjacent vertebral endplate regions have been substantially preserved. That is not to say that the endplates must be pristine. Rather, the implant as contemplated in the preferred embodiment described herein is designed to be used in a disc space where a structurally significant amount of the endplate subchondral region remains. A preferred implant of the present invention is deployed by rotating it 90 degrees about its long axis such that a body portion of the implant contacts and supports the adjacent vertebral endplate regions while projecting members, for example fins or blade-like projections, are driven and then extend into the deeper interior bone of those vertebral bodies.

It is an object of the present invention to provide an improved spinal fusion implant configured to permit vertebral body to vertebral body fusion through the implant. The implant is inserted between adjacent vertebral bodies and then rotated 90 degrees into place without over-distracting the vertebral bodies apart while penetrating the vertebral endplates to access the underlying bone vascularity and to lock the implant into position, thereby stabilizing the adjacent vertebral bodies relative to the implant and relative to each other. The phrase "without over-distraction" is defined as distracting the vertebral bodies in the range of elastic deformation and short of plastic deformation and tissue failure. To avoid any ambiguity regarding the phrase "without over-distraction," this phrase and the individual words contained therein are not being used as they may be in their normal or ordinary use, but are being used as defined in this application only.

It is a further object of the present invention to provide an improved interbody spinal fusion implant that may, but need not necessarily, be inserted without the need to drill a bore across the disc space and into the adjacent vertebral bodies, thereby substantially preserving the endplate regions of the adjacent vertebral bodies while still providing access to the subchondral vascular bone vital to interbody fusion.

Additional objects and advantages of the invention will be set forth in part in the description that follows, and in part will be evident from the description, or may be learned by practice of the invention. The objects and advantages of the invention will be realized and attained by means of the elements and combinations particularly pointed out in the appended claims.

The following description is intended to be representative only and not limiting and many variations can be anticipated according to these teachings and are included within the scope of this inventive teaching.

To achieve the foregoing objects, and in accordance with the present invention, as embodied and broadly described herein, there is provided an improved interbody spinal fusion implant for insertion across a disc space between adjacent vertebral bodies of a human spine. In a first embodiment, the implant has a body having an insertion end, side walls, upper and lower walls, and a cross-section wherein the side walls intersect the upper and lower walls at two diametrically opposed corners and two diametrically opposed arcs. The implant also has one or more fin-like protrusions extending outwardly from the upper and lower walls so that when the implant is rotated approximately 90 degrees into its final position between the vertebral bodies, the protruding fins penetrate the endplates of the adjacent vertebral bodies. The implant can be configured so as to have only a single direction of rotation or to be symmetrically rotatable. When the implant is configured so as to be rotatable in either direction about its long axis, i.e. it is symmetrical, then the junctions of the side walls to the upper and lower walls will preferably each be arced. As used herein, the term "side walls" refers to those portions of the implant that extend between the adjacent vertebral bodies after the implant has been rotated into its final position within the disc space. The "upper" and "lower" walls refer to those portions of the implant that contact the vertebral bodies cephalad and caudad, respectively, after the implant is rotated into its final position within the disc space and which surfaces bear the vertebral bodies penetrating fin-like projections.

There are numerous claimed variations on the above-described implant. By way of example only, the side walls and upper and lower walls, respectively, may be generally parallel to one another. The side walls may physically contact the adjacent vertebral bodies upon initial insertion between the vertebral bodies before the implant is rotated into its final position. The side and/or upper and lower walls may be configured with openings to allow bone to grow therethrough, and the implant may have a hollow portion that can be loaded with a fusion-promoting material to promote fusion between the adjacent vertebral bodies. The upper and lower walls may be angled in various directions to one another to account for lordosis in the spine, and/or may be contoured to match the natural contours of the endplates of the adjacent vertebral bodies.

The implant can be made of any material appropriate for human implantation within the spine and of sufficient strength to work for the intended purpose. Such materials include, but are not limited to, cortical bone, bone composite, plastics, carbon-fiber or other composites, ceramics, surgical grade implant quality metals such as titanium and titanium alloys, tantulum, and chomemoly alloy. The implant may further comprise of bioresorbable material and of materials that are bioactive or induce the production of bone vital for fusion. Such materials may be within the material of the implants, contained within the structure of the implant, or be a coating or treatment to the implant. Such materials include, but are not limited to, bone morphogenetic proteins, genetic factors, (genetic material coding for the production of bone) and converting factors to stimulate the formation, recruitment, and/or activity of osteoblasts, or other cells or cellular mechanism for bone production.

The diametrically opposed junctions are preferably arcuate, and more preferably arcs that can be configured in different ways. For example, the arcs may be arcs of radii and may further be each of the same radius. Or, the arcs may each be chords of the same circle, or quadrants of a circle. Likewise, the other of the diametrically opposed junctions may be corners, such as can form right angles. The other opposed junctions, alternatively, can be relieved, chamfered, or radiused as when it is desired to have an implant that can be rotated in either direction about its longitudinal axis.

The fins also may have a number of different configurations. Alternative fin configurations include protrusions having different heights, equal height, or varying lengths along a portion of the length of the implant as measured from either a central longitudinal axis passing through the implant or the upper and lower surfaces of the implant body from which the fins project. The fins or protrusions may also be of varied or constant thickness, or varied or constant spacing from fin to fin. The fin or protrusion may have a sharp leading edge and/or outer surface to facilitate cutting into the vertebral endplate region upon rotation of the implant and in a preferred configuration go from a knife-like, ramped, thin, and sharpened leading edge to a thickened and blunt trailing end. To avoid any ambiguity regarding what is intended as a body having upper and lower surfaces and fins projecting therefrom as used herein, an implant even if so formed so as to obscure the distinction between the upper and lower surfaces and projecting fins would nevertheless be within the scope of the terms and claims of the present application. It is understood that in this case there is still an area between the fins that would come to lie in support of each of the vertebral bodies at the surfaces adjacent the disc space, and such an implant is within the scope of the present invention.

The implant of the present invention need not be used alone. Rather, the implant can be used with a complementary implant to provide additional stability and fusion promotion. This complementary implant is novel in and of itself and comprises an alternative embodiment of the present invention. For example, a second implant of the type previously described can be rotated into place after the first implant, either in the same direction (i.e. clockwise or counterclockwise) as the first implant or preferably in an opposite direction from that of the first implant. The direction of rotation of the implant depends upon the location of the diametrically opposed junctions that are preferably arcs of radii. Those implants of a preferred embodiment having a single direction of rotation configuration, rotate in the direction that causes the arcs of radii, rather than the corners, to engage the endplates when the implant has been rotated approximately 45 degrees, so as to utilize the geometrical configuration of the arcs of radii to avoid over-distraction.

Once two such implants have been inserted into a disc space intermediate adjacent vertebral bodies, there may be room to insert a third specialized implant between those two but insufficient room to allow for the rotation of that third implant for its seating. Therefore, a preferred novel, complementary third implant has in its preferred embodiment ratchetings on its upper and lower surfaces to engage the endplates of the adjacent vertebral bodies and thereby gain stability within the disc space, and preferably may also have ratchetings on its sides to mate with similarly spaced ratchetings on the side walls of the first and second implants so as to be locked into place by each of those implants, which themselves are locked into the adjacent vertebral bodies. It is anticipated that the implants can interdigitate in other ways for similar purpose. The third implant may force the first and second implants further apart thereby trapping itself in place and enhancing the stability of the other two implants as well as the adjacent vertebral bodies relative to the implants and to each other. While ratchetings are preferred, other surfaces such as knurling or other structures to mechanically interdigitate the implant to the adjacent vertebral bodies and to the adjacent implants are included within the scope of the present teaching.

The present invention also includes a method for deploying at least one of the subject interbody spinal fusion implants across a disc space and into adjacent vertebral bodies within a human spine. The method comprises the steps of: removing at least a portion of the disc from between the adjacent vertebral bodies from vertebral endplate to adjacent vertebral endplate, and to a depth at least as great and preferably greater than the length of the implant, and to a width at least as great as the height of the implant as measured from fin tip to opposed fin tip where maximum for that implant; providing a first implant having an insertion end, a trailing end, side walls and upper and lower walls bearing protrusions, which protrusions are preferably, but not necessarily, in the form of fins extending outwardly from the opposed upper and lower walls. Preferably, the upper and lower walls have at least one, or alternatively a plurality of, openings passing therethrough so as to allow for the growth of bone in continuity from one of the adjacent vertebral bodies to the other of the adjacent vertebral bodies through the spinal fusion implant. The implant includes a cross-section with the side walls intersecting with the upper and lower walls at junctions, which preferably are two diametrically opposed arcuate portions. The method also includes the steps of inserting the implant by linearly advancing it between the adjacent vertebral bodies with the side walls facing the endplates of the adjacent vertebral bodies, and then rotating the implant 90 degrees about its long axis so that the surface projections extending from the upper and lower walls are driven into the bone of the adjacent vertebral bodies into a deployed position such that the fins are driven and penetrate the end plates of the adjacent vertebral bodies. When the implant is deployed, the upper and lower walls from which the fins extend will then be placed into contact and support through the endplate regions the adjacent vertebral bodies.

Another embodiment of the present invention includes the steps of removing disc material as described; attaching the implant to a hand-held driver instrument; retracting any bodily tissues including, but not limited to, neurological structures, vascular structures, and bodily organs to provide clear access to the space created; attaching to the implant a hand-held insertion instrument capable of engaging the implant to provide for both linear advancement and rotation; inserting the implant by linearly advancing the implant in the space created between the adjacent vertebral bodies with the side of the implant adjacent the vertebral endplates to a depth sufficient so the implant does not protrude from the spine; rotating the implant by use of an instrument and preferably the insertion instrument so that the preferred junctions of opposed arcuate portions contact the adjacent vertebral bodies; continuing to rotate the implant so that the fin-like projections of the upper and lower walls are driven through the adjacent surfaces of the adjacent vertebral bodies until the implant rotates approximately 90 degrees; and disengaging the insertion and/or rotation tool without derotation of the implant.

The method preferably includes the steps of providing a second implant having an insertion end, a trailing end, side walls and upper and lower walls with outwardly extending fins, at least the upper and lower walls having openings which pass therethrough that are sufficiently sized and configured to allow for the growth of bone in continuity therethrough from vertebral body to vertebral body in a structurally meaningful way so as to significantly bear load from vertebral body to vertebral body, the second implant having a cross-section with the side walls intersecting the upper and lower walls at junctions, which preferably are two diametrically opposed arcuate portions; inserting the second implant between the adjacent vertebral bodies with the side walls directed toward the adjacent vertebral bodies; and then rotating the second implant 90 degrees into a deployed position such that the upper and lower walls then contact and support each of the adjacent vertebral endplate regions while the fins, extending from the upper and lower walls, are then penetrably driven through the vertebral endplates.

As a substep of that method, the first implant may be deployed by rotating it 90 degrees in a first direction while the second implant may be deployed by rotating it in either the same direction or preferably in the opposite direction.

The method may further comprise lateralizing (more lateral) the first and second implant to provide a space between the first and second implants. The method may still further comprise placing within that space a third implant different in structure from the first and second implants in that while it is designed to be inserted by linear advancement, it is not designed to be rotated into place. The specialized third implant may include protrusions (ratchetings) on its outer walls so as to engage the implant to the adjacent vertebral bodies and to engage the third implant to the first and second implants. This specialized third implant preferably has upper and lower walls for contacting each of the adjacent vertebral bodies. The upper and lower walls have at least one opening to allow for the growth of bone in a mechanically meaningful way in continuity from a first adjacent vertebral bodies through the implant to the second of adjacent vertebral bodies. Further, a substep preferably for use when the implant is made of a material such as cortical bone, carbon fiber or any material less strong than titanium alloy, includes the use of a rotary broach or tap to provide slits in the vertebral endplates through which the fins are guided.

When the first and second implants rotate in opposite directions away from each other, the fins cut a path through the surfaces of the adjacent vertebral bodies longer than that occupied by the implant itself when deployed. This facilitates the implants being slid apart without tipping over, twisting,,or moving forward or back as the fins slide sideways relative to their long axis from more central to more lateral. In a preferred method, the present disc material including portions of the very strong annulus fibrosus resist such implant lateralization and tend to urge the first and second implants back centrally. Thus, the third implant is wedging apart the other two implants and in this situation obtains for itself and provides to the other implants and to the adjacent vertebral bodies an extra measure of stability.

It is to be understood that both the foregoing general descriptions and the following detailed description are exemplary and explanatory only and are not restrictive of the scope of the invention, which scope is defined solely by the appended claims.

The accompanying drawings, which are incorporated in and constitute a part of this specification, illustrate several embodiments of the invention and, together with the description, serve to explain the principles of the invention.

BRIEF DESCRIPTION OF THE DRAWINGS

FIG. 16A is a top view of a clockwise rotation spinal fusion implant and counter-clockwise rotation spinal fusion implant spaced apart from one another with a third, non-rotatable spinal implant positioned to be inserted there between.

DESCRIPTION OF THE PREFERRED EMBODIMENTS

Figure 1:
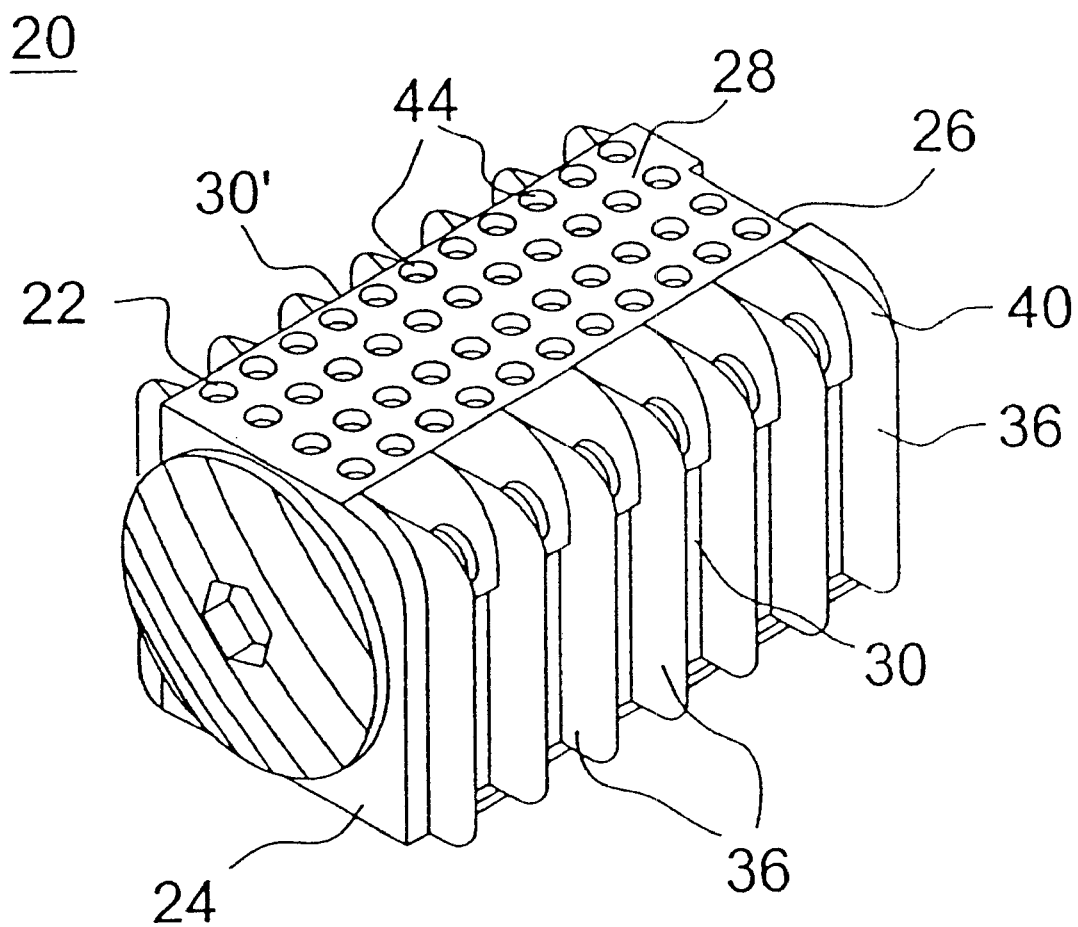
FIG. 1 is a perspective view of one embodiment of a spinal fusion implant incorporating some of the features of the present invention, which implant is oriented in an initial insertion position and configured for clockwise rotation into its final, deployed position between adjacent vertebral bodies.

Reference will now be made in detail to the present preferred embodiments of this invention, examples of which are illustrated in the accompanying drawings. Similar reference numbers such as 28, 28' will be used throughout the drawings to refer to similar portions of the same implant.

With reference to FIG. 1 and FIGS. 2A–2F, an interbody spinal fusion implant in accordance with a preferred embodiment of the present invention is indicated generally as 20. The implant has a body 22 having an insertion end 24, a trailing end 26, opposed side walls 28, 28' and opposed upper and lower walls 30, 30'. Body 22 has a cross section with side walls 28, 28' intersecting the upper and lower walls 30, 30' at junctions that are preferably two diametrically opposed corners 32, 32' and two diametrically opposed arcs 34, 34'. Fin-like projections 36, 36' extend outwardly from respective ones of upper and lower walls 30, 30' and are adapted to penetrate the vertebral endplates of the adjacent vertebral bodies upon rotation of implant 20 while the upper and lower walls 30, 30' support the vertebral endplates of those adjacent vertebral bodies.

A brief discussion of a preferred method of use of an embodiment of present invention implant will serve to highlight the function of the structural features of implant 20.

Figure 3A:
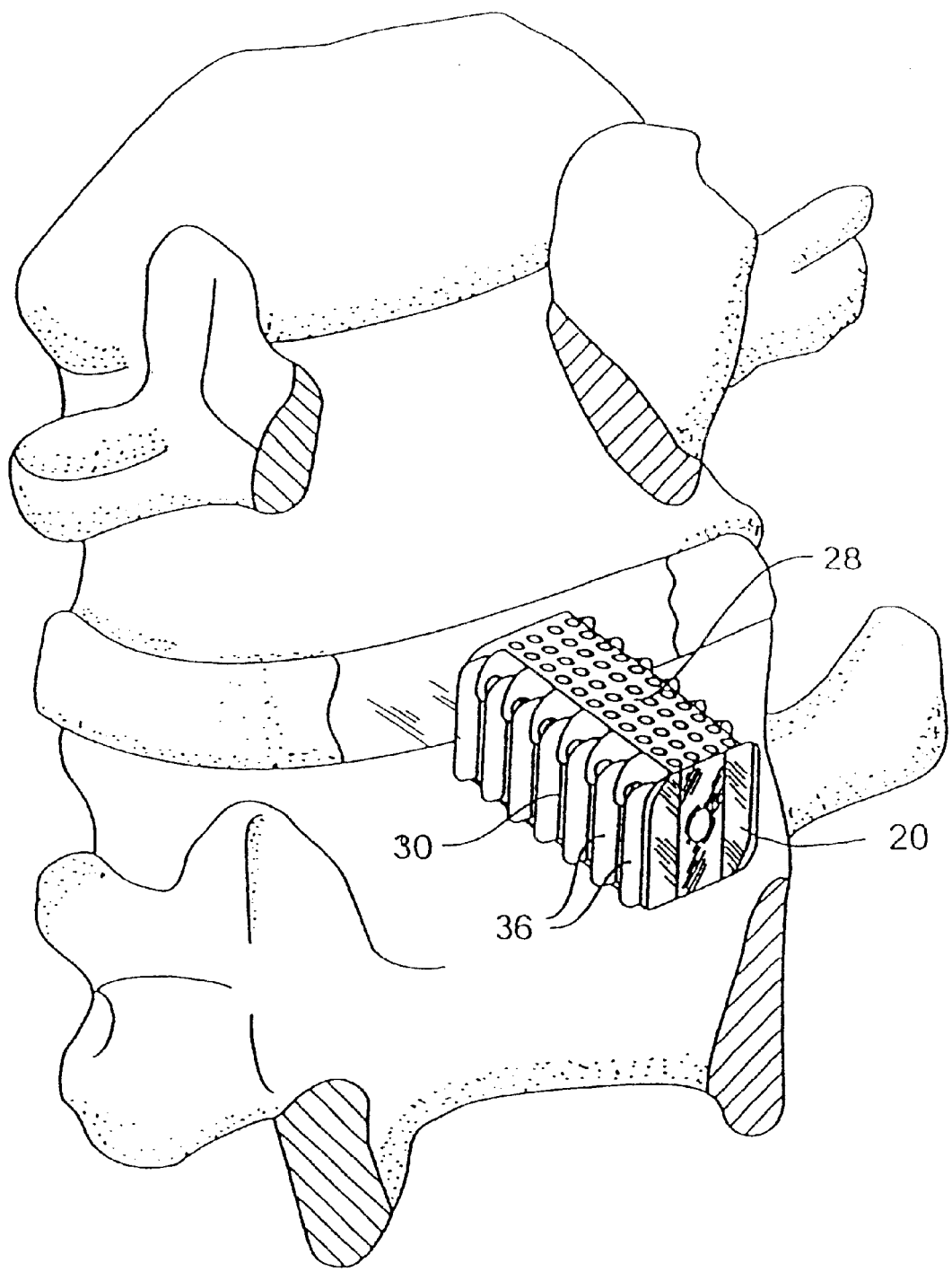
FIG. 3A is a perspective view of portion of a spinal segment (two vertebra and an interposed disc space) with an embodiment of an implant of the present invention oriented in an initial insertion position.
Figure 3B:
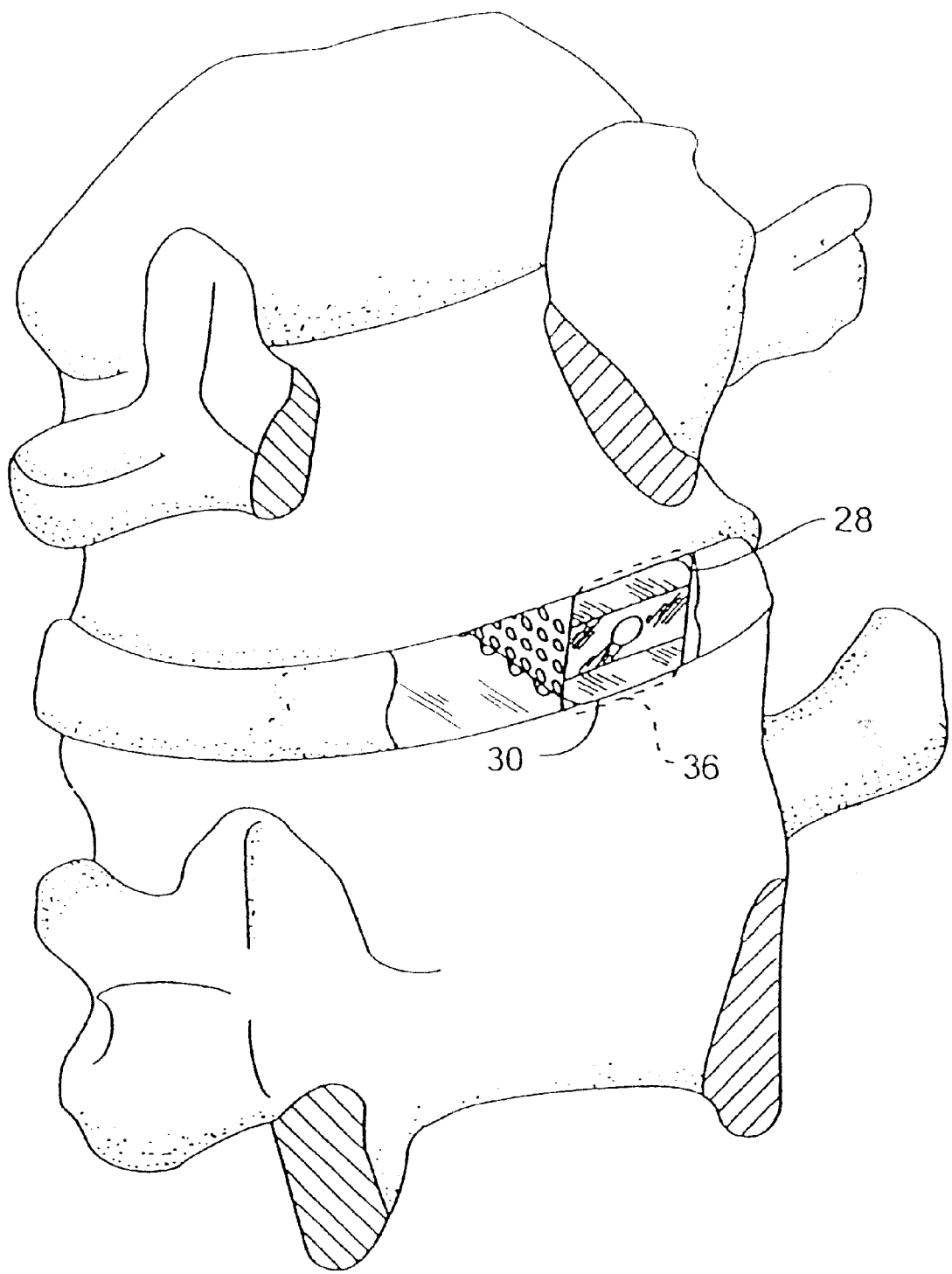
FIG. 3B is a perspective view of the spinal segment of FIG. 3A with the implant of FIG. 3B oriented in a deployed position and two of the fin-like projections of the implant show in dashed lines.

With reference to FIG. 3A, and with the disc space optimally distracted, implant 20 is advanced linearly until fully contained within the disc space and oriented so that side walls 28, 28' are opposed to the endplates of the vertebral bodies adjacent the disc space. Arcs 34, 34' of implant 20 assure that as implant 20 is rotated 90 degrees about its longitudinal axis, the diagonal of this generally cuboid, trapezoid, or otherwise shaped implant body, will not have a dimension substantially greater than the height of body 22 of implant 20, that "height" being the distance between upper and lower walls 30, 30' of implant 20. This feature, as best shown in FIG. 3B, allows upper and lower walls 30, 30' to be placed into contact with and to support the vertebral endplates of the adjacent vertebral bodies without over-distracting the disc space or damaging the vertebral bodies. To avoid any ambiguity regarding the phrase "without over-distraction," this phrase and the individual words contained therein are not being used as they may be in their normal or ordinary use, but are being used as defined in this application only.

Figure 3C:
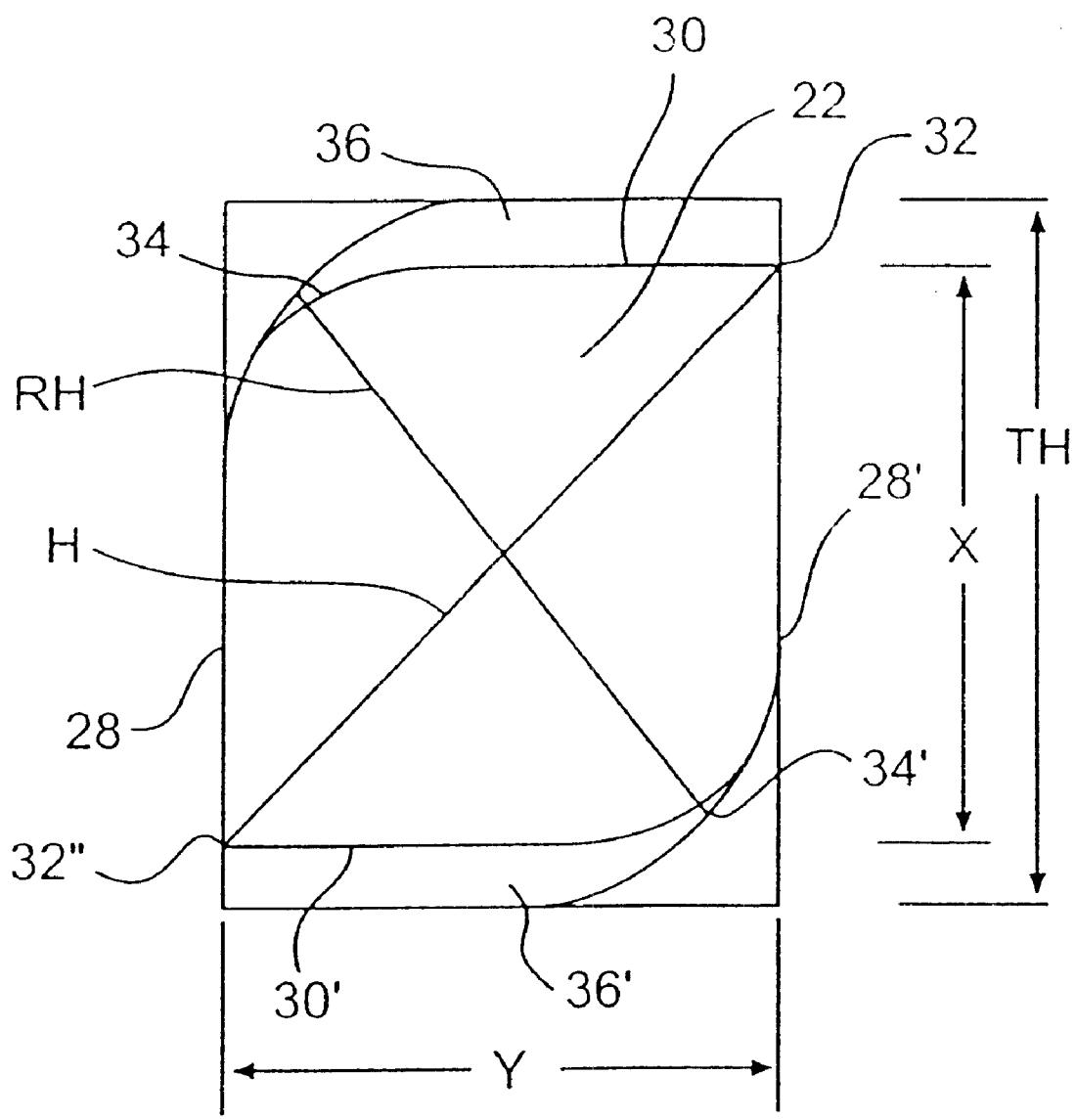
FIG. 3C is a schematic representation of a geometric configuration of a cross-section of the body of the implant of FIGS. 1 and 2.
Figure 4:
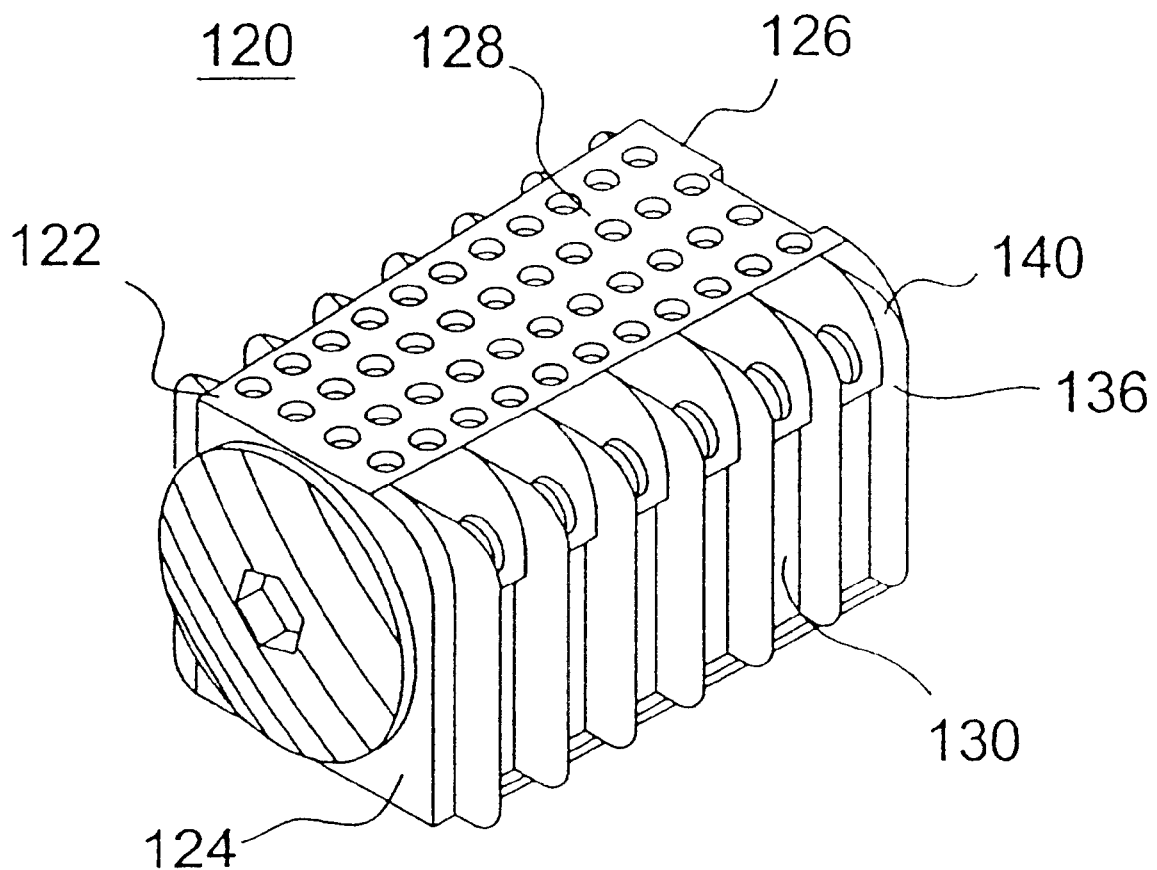
FIG. 4 is a perspective view of an alternative embodiment of a spinal fusion implant of the present invention oriented in an initial insertion position and configured for clockwise rotation within the disc space, the top and bottom walls thereeof being tapered relative to one another for inducing angulation of the adjacent vertebral bodies.

As best shown in the schematic representation of a geometric configuration of a cross-section of a preferred embodiment of body 22 of implant 20 in FIG. 3C, implant 20 has opposed side walls 28, 28', upper and lower walls 30, 30', a height "X", a width "Y", a hypotenuse "H", and a reduced or modified hypotenuse "RH". Reduced hypotenuse RH is much closer to height X of implant 20 than unmodified hypotenuse H. While height X is depicted as being greater than width Y, this schematic is shown by way of example and not limitation, such that it is to be understood that height X could also be equal to or slightly less than width Y along the length of implant 20 or any portion thereof.

Reduced hypotenuse RH is significantly less than hypotenuse H in this embodiment of the present invention to allow for the rotation of implant 20 from the an insertion position to a deployed position without over-distraction occurring during this process. While reduced hypotenuse RH is illustrated as being arcuate in this preferred embodiment, the configuration of body 22 of implant 20 to form reduced hypotenuse RH can take many forms, including arcuate portions, a radius, a chamfer, a series of angled surfaces, or any other shape so long as a reduced hypotenuse RH of sufficient dimension for the intended purpose of the present invention results therefrom. Reduced hypotenuse RH has a diagonal that does not significantly exceed the height and may be equal to or less than height H of body 22 of implant 20. Reduced hypotenuse RH is preferably substantially the same as the height H of body 22, and in one preferred embodiment reduced hypotenuse RH has a length within 10% of the height H of body 22. Reduced hypotenuse RH also has a diagonal that is less than implant 20 total height "TH" including fins 36, 36', and more preferably markedly less than the total height TH of implant 20 including fins 36, 36'.

A hypotenuse (true hypotenuse) is a side of a right-angled triangle opposite the right angle. When reference is made herein to a hypotenuse or a reduced hypotenuse, reference is being made to the diagonal dimension of a theoretical line between diagonally opposed points of the implant overlying the true hypotenuse. Side walls 28, 28' and upper and lower walls 30, 30' do not need to intersect, but in fact may have a relief, radius, or chamfer by way of example, to form a theoretical line overlying and shorter than a true hypotenuse of a right-angled triangle formed with sides corresponding to side wall 28' and lower wall 30', respectively. As shown in FIG. 3C, hypotenuse H represents the dimension of a line between points 32 and 32' on body 22 across a right angle that would be formed if side wall 28' and lower wall 30' were to continue in their respective planes to intersect at a right angle as illustrated by X and Y in FIG. 3C. Reduced hypotenuse RH represents the dimension of a line between points 34 and 34' on body 22 across a right angle that would be formed by the intersection of side wall 28 and lower wall 30' because of the radiused junction at the corners of a theoretical right-angled triangle. While reference has been made to a hypotenuse as being the side across a right angle, if the side walls and upper and lower walls were to intersect at an angle other than a right angle, for purposes of this application, a long side of the triangle formed by an angle other than 90 degrees is still referred to herein as a hypotenuse.

An embodiment of the present invention where reduced hypotenuse RH is slightly greater than height X offers the advantage of an over-center effect that locks implant 20 into place. In this instance, once implant 20 rotates past the diagonal of reduced hypotenuse RH, more force would be required to rotate it back from the final deployed position to its insertion position than in an embodiment where reduced hypotenuse RH is equal to or less than height H.

Fins 36, 36' are of greater height than the implant body height as measured between upper and lower walls 30, 30'. Fins 36, 36' come to reside within the interior of the adjacent vertebral bodies after being driven through the endplates by the act of rotation. This penetration of fins 36, 36' into the interior, cancellous region of the vertebra allows the implant to access the vascular bone beneath the endplate and further provides for significant stability of implant 20 as each fin 36, 36' acts as an anchor within the body of the vertebra. It can be seen that the surface area of the vertebral bodies in contact with implant 20 is greatly enhanced by fins 36, 36' as compared to a flat surface.

Upper and lower walls 30, 30' of implant 20 are configured to support the bone of the vertebral endplate region. When implant 20 is inserted into an already distracted disc space corresponding in height to the height of the fusion implant body 22, fins 36, 36' protruding from implant body 22 will be driven during rotation through the endplates and into the vertebral bodies. This cutting action of fins 36, 36' can further be enhanced by shaping the leading edges of fins 36, 36' so they are pointed, sharpened, or both. The leading edge of fins 36, 36' may additionally have a ramped or sloped profile.

From the structure of implant 20 it can be appreciated that upper and lower walls 30, 30' may be configured with a distance between them corresponding to the optimally distracted height of the disc space. The upper and lower walls 30, 30' may be formed with surface configurations that conform to the vertebral endplates of the adjacent vertebral bodies to provide optimum contact and support between the endplates and the implant. Upper and lower walls 36, 36' also have at least one, and alternatively a plurality of, openings therethrough so as to allow for the growth of bone in continuity from adjacent vertebral bodies to adjacent vertebral bodies through the implant to permit the vertebral bodies to fuse to one another. Implant side walls 28 and 28' can have none, one or preferably a plurality of openings.

Figure 2A:
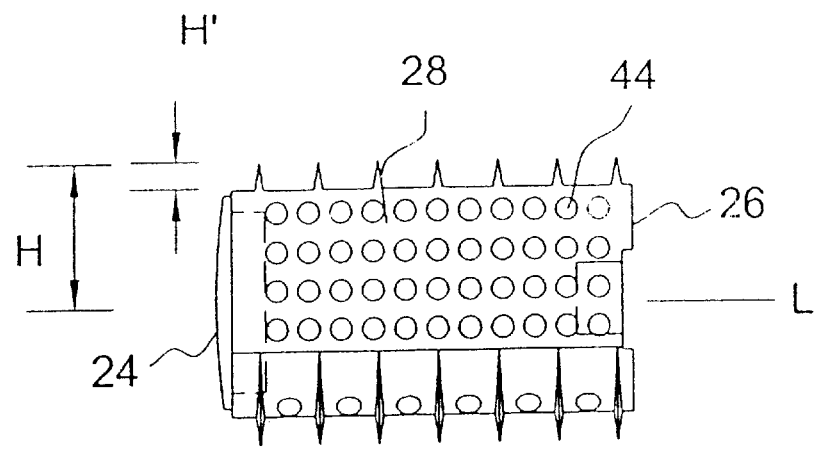
FIGS. 2A–2E are side, lower, upper, trailing end, and insertion end views, respectively, of the implant of FIG. 1 as would be observed when the implant is in a final, deployed orientation between vertebral bodies.
Figure 2B:
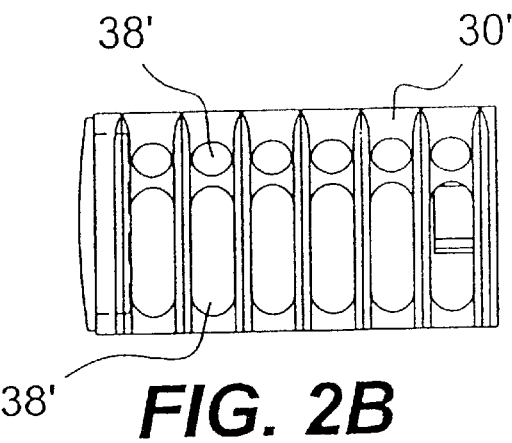
Figure 2C:
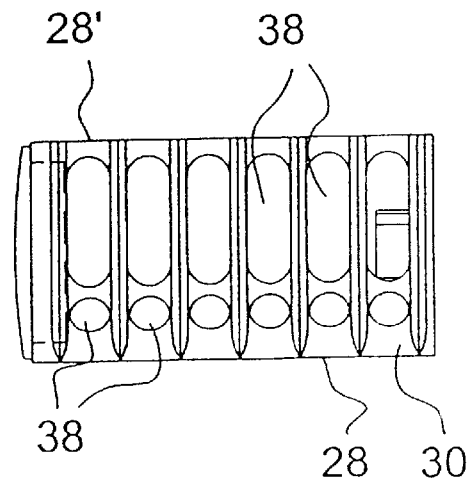

As shown in FIG. 1 and FIG. 2A, side walls 28, 28' preferably have a distance between them so that they contact the adjacent vertebral bodies upon initial insertion of implant 20 into the spine. Each of side walls 28, 28' lie generally in a plane and, in a preferred embodiment, side walls 28, 28' are generally parallel to one another.

Figure 2D:
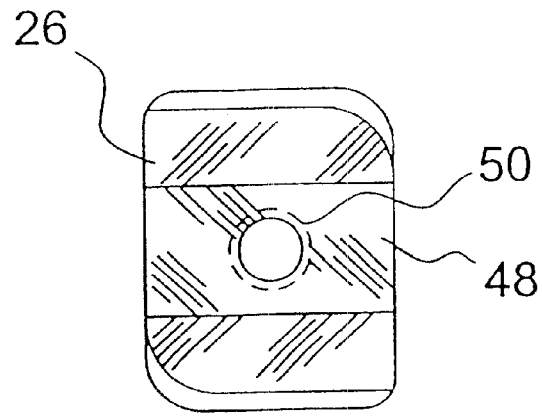
Figure 2E:
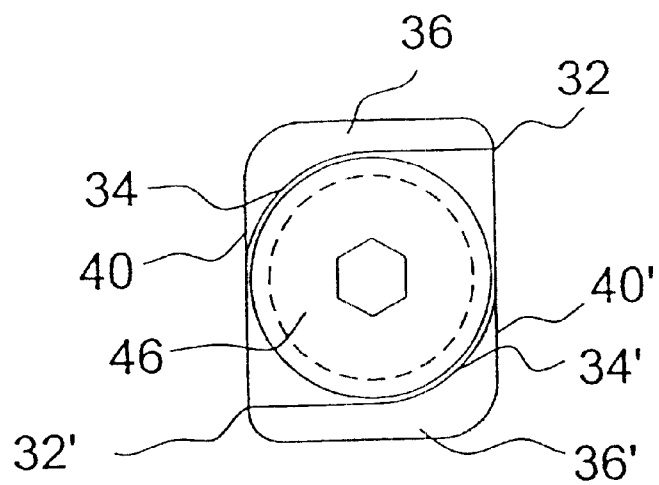
Figure 2F:
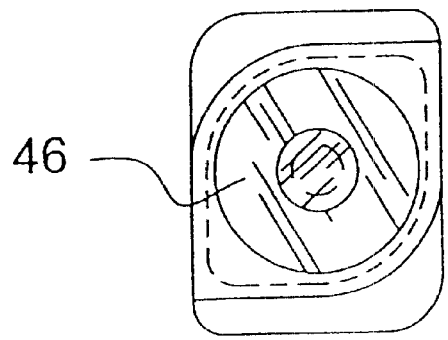
FIG. 2F is an insertion end view of the spinal implant of FIGS. 2A–2E illustrating an opening in the trailing end and for providing access to a hollow portion.

Two diametrically opposed arcs 34, 34' are preferably, but not necessarily, formed as arcs of radii. More preferably, each of the opposed arcs 34, 34' are of the same radius as shown in FIG. 1 and FIG. 2E and more preferably are arcs of the same circle. The two diametrically opposed arcs 34, 34' may also include quadrants of the same circle. The distance between opposed arcs 34, 34' preferably approximates the distance between the upper and lower walls 30, 30' such that, when implant 20 is rotated from an initial insertion position toward a final deployed position, no over distraction of the space between the adjacent vertebral bodies occurs and no damage to the vertebral bodies occurs.

Fins 36, 36' have a height H measured from the longitudinal central axis L of implant 20. In a first embodiment, height H may be substantially uniform along a portion or the entire length of implant 20. Alternatively, fins 36, 36' may have height H' measured from upper and lower walls 30, 30' that is substantially constant along the length of implant 20. Other variations on the height and configuration of the fins are readily appreciated by those of skill in the art, i.e., spine surgeons, and are incorporated as part of the present invention. Fins 36, 36' preferably have a sharp leading edges 40, 40' for penetrating the vertebral endplates upon rotation of implant 20. The leading edges 40, 40' may also be pointed, and/or ramped. Fins 36, 36' may be sharpened along any portion of their length so as to facilitate the penetration of fins 36, 36' through the vertebral endplates and into the interior, cancellous region of the vertebral bodies. Fins 36, 36' may be thickened at their trailing end to more tightly lock implant 20 into place. Fins 36, 36' may be of different shapes and arrangements. By way of example only and not limitation, fins 36, 36' may be in the shape of fin-like projections evenly spaced along at least a portion of the upper and lower walls 30, 30'. It is also contemplated within the scope of the present invention that fins 36, 36' may be portions ID or segments of a helix, or have uneven spacing along the length of the implant. Fins 36, 36' may have any of a variety of shapes suitable for their intended purpose as stated herein.

Implant 20 of FIG. 1 is configured to have a single direction of rotation. It can be seen in this exemplary embodiment, as best shown in FIGS. 3A and 3B, that in an appropriately distracted space, rotation of implant 20 in a counterclockwise direction would be blocked due to the fact that the length of the diagonal of implant 20 between the corners 32, 32' exceeds the height of the disc space. In contradistinction, the implant may be rotated in a clockwise direction because the diagonal between arcs 34, 34' is less than or equal to the length of the disc space.

Body 22 of implant 20 preferably includes a hollow portion 42. Hollow portion 42 is adapted to contain fusion promoting material including, but not limited to, bone, in any of its varied forms, hydroxyapatite, coral, bone morphogenetic proteins, and agents with the ability to induce cells to become osteoblasts or to make bone. The implant of the present invention can be made of any material suitable for its purpose and appropriate for implantation in the human spine. Such materials include, but are not limited to, bone itself and particularly human cortical bone as it is obtainable from a cadaver from such areas as the femur, so long as the bone material possesses sufficient strength for the intended purpose. The implants of the present invention can be made of a novel material including an artificial composite of bone and a bioresorbable (broken down and absorbed by the body over time) plastic e.g., from the lactide family including lactones, polylactones, galactone, and so forth, or any such plastic that can be utilized to bind the bone fragments together so that the resultant material is of sufficient strength and for a long enough period of time to work for the intended purpose of being a material for interbody fusion through the implant spinal fusion device. Much like carbon fiber composite, in such a novel material the bone would preferably, but not necessarily, be human bone fragmented into preferably cortical strips having lengths significantly greater than their width so as to take the form of fibrils. These fibrils either randomly disposed, organized in layers or woven together into sheets or pads or meshes would be combined with resorbable plastic to form the material of the implant. The implant could either be molded from the material, machined from the material, or a combination of both.

As previously stated, implant 20 has at least one and, alternatively, a plurality of openings through upper and lower walls 30, 30' herein shown as openings 38, 38' passing through the body and in communication with hollow portion 42. These openings provide a passageway through implant 20 and through the upper and lower walls 30, 30' of implant 20 to allow for the growth of bone in continuity from one adjacent vertebral body through the implant to the other adjacent vertebral body. Side walls 28, 28' may also include openings 44, 44' passing therethrough in communication with hollow portion 42. It shall be readily appreciated that openings 38, 38' in upper and lower walls 30, 30', as well as openings 44, 44' in side walls 28, 28', may have any shape, size, configuration, or distribution suitable for the intended purpose of permitting a fusion to take place through the implant. In the present embodiment, at least some of openings 38, 38' and 44, 44' are macroscopic in size, i.e., greater than 1.0 mm in dimension across. However, as will be discussed in more detail in regard to the embodiment of FIGS. 14 and 15A–15D, an implant of the present invention may also comprise extensive surface openings of less than 1.0 mm so as to approximate the structure of human cancellous bone or an implant can combine these features. The implant of the present invention may also include openings 38, 38' and 44, 44' that are microscopic in size, that is, less than about 40 □m. Microscopic is defined herein as being of a size sufficiently small that magnification is required to appreciate the fine detail of the structure and as used herein is less than 1 mm in maximum dimension.

Implant 20 preferably includes a cap 46 with a thread that threadably attaches to insertion end 24 of implant 20. Cap 46 is removable to provide access to hollow portion 42, such that hollow portion 42 can be filled (under compressive load if desired) with any natural or artificial osteoconductive, osteoinductive, osteogenic, or other fusion enhancing material. Some examples of such materials are bone harvested from the patient, or obtained elsewhere, or bone growth inducing material such as, but not limited to, hydroxyapatite, hydroxyapatite tricalcium phosphate, bone morphogenetic proteins, or genes coding for the production of bone.

Cap 46 and/or implant 20 may be made of any material appropriate for human implantation including metals such as cobalt chrome, stainless steel, titanium, plastics, ceramics, composites and/or may be made of, and/or filled with, and/or coated with a bone ingrowth inducing material such as, but not limited to, hydroxyapatite or hydroxyapatite tricalcium phosphate or any other osteoconductive, osteoinductive, osteogenic, or other fusion enhancing material, including bone morphogenetic proteins or other genetic material (genes coding for the production of bone) to stimulate the formation of bone making cells and/or the formation of bone by cells. Cap 46 and implant 20 may be partially or wholly bioabsorbable. Cap 46 is not limited, however, to a threaded coupling, which is offered only by way of example. Implant 20 and cap 46 may each be adapted to cooperatively engage the other in any manner suitable for the intended purpose and as known to those skilled in the art. The implant does not require an end opening and may in various embodiments, including a single opening being easily loaded through the opening. Cap 46 may also be configured to cooperatively engage a driver for engaging cap 46 to implant 20 or for inserting and rotating implant 20 into the disc space and adjacent vertebral bodies. Cap 46 may also be perforate so as to retain fusion promoting substances within implant 20 while providing for vascular access and growth therethrough.

In a preferred embodiment, for use in the lumbar spine when oriented front to back or back to front, implant 20 has an overall length in the range of approximately 20 mm to 34 mm with 26 mm to 28 mm being the preferred length. Body 22 of implant 20, as defined by the distance between the upper and lower walls 30, 30', has a height from about 6–20 mm when for use in the lumbar spine, which height can vary over the length of the implant. Fins 36, 36' have a preferred height when measured from body 22 in the range of from 1–5 mm. Side walls 28, 28' are preferably spaced apart from each other a distance in the range of from 6–20 mm. Fins 36 extend from upper and lower walls 30, 30' such that the distance measured from the tip of fin 36 to the tip of fin 36' is greater than the distance between upper and lower walls 30, 30'. An implant for use in the cervical spine preferably has a length from 10–22 mm, a body height from 5–12 mm, a fin height from 0.5–2.5 mm, and a body width from 5–12 mm.

A preferred embodiment of the present invention includes means for engaging an implant driver. Preferably, but not by way of limitation, the engaging means is located at trailing end 26 of implant 20 allowing for the full loading of implant 20 prior to insertion. It is also preferable that the driver engaging means allows implant 20 to be secured to the implant driver such that it can be pulled or pushed as well as rotated without inadvertent disengagement of the driver. One such engaging means is shown in FIG. 2D wherein implant 20 has a recessed slot 48 formed at its trailing end 26 for receiving insertion instrumentation. Recessed slot 48 has a threaded opening 50 for threadably attaching implant 20 to instrumentation for use in inserting implant 20. Numerous other types of engaging means will be readily contemplated by those of skill in the art, and such alternative mechanisms are within the scope of the present invention.

Figure 5A:
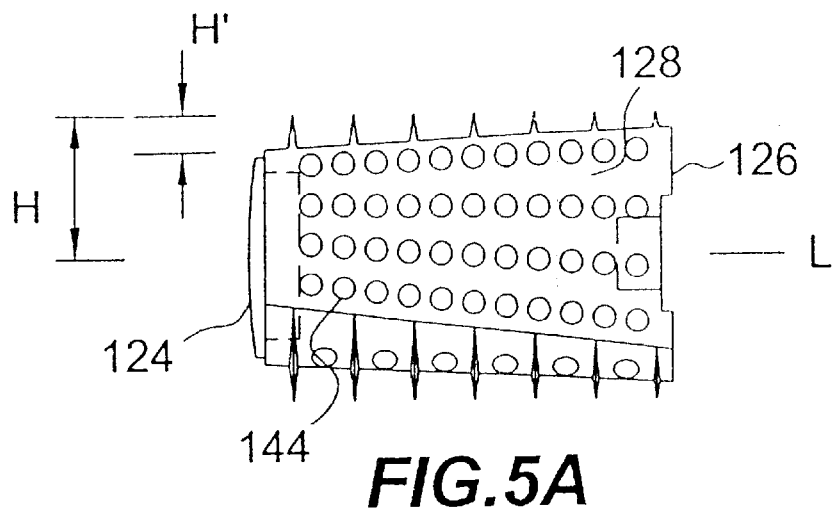
FIGS. 5A–5E are side, lower, upper, trailing end, and insertion end views, respectively, of the implant of FIG. 4 in a deployed orientation.
Figure 5B:
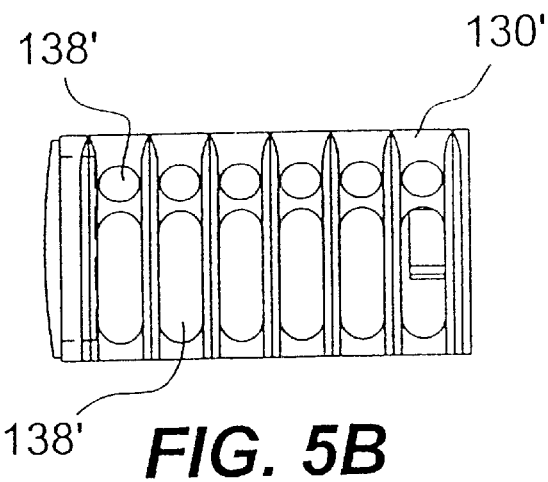
Figure 5C:
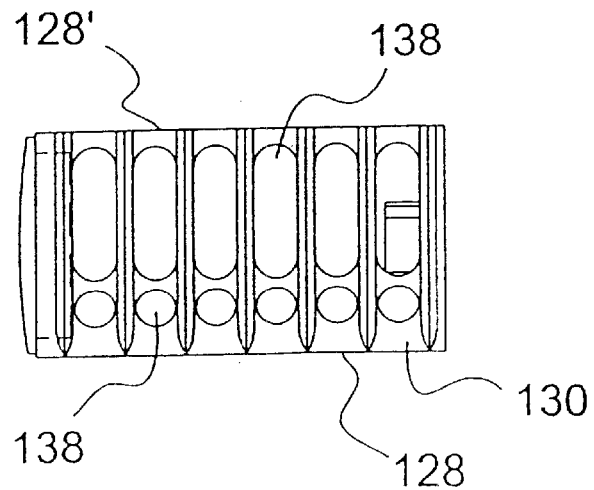
Figure 5D:
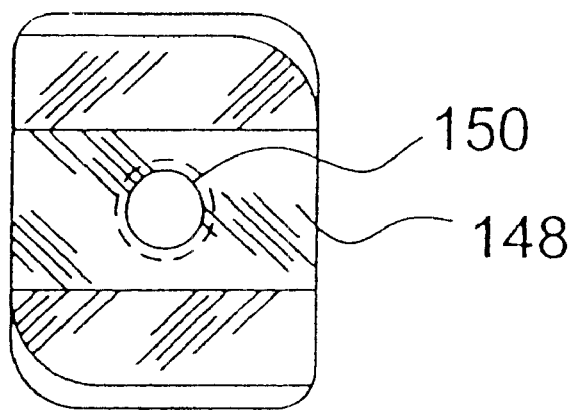
Figure 5E:
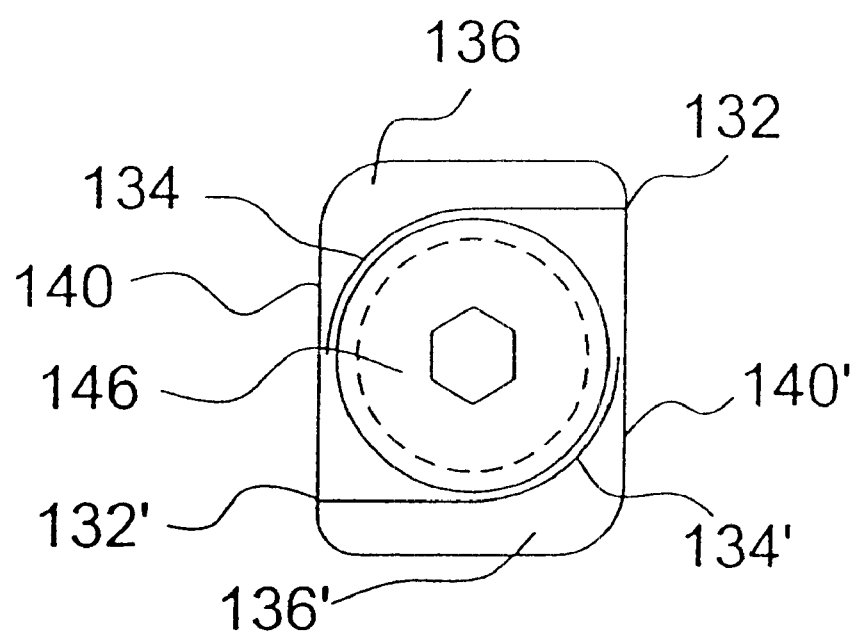
Figure 6:
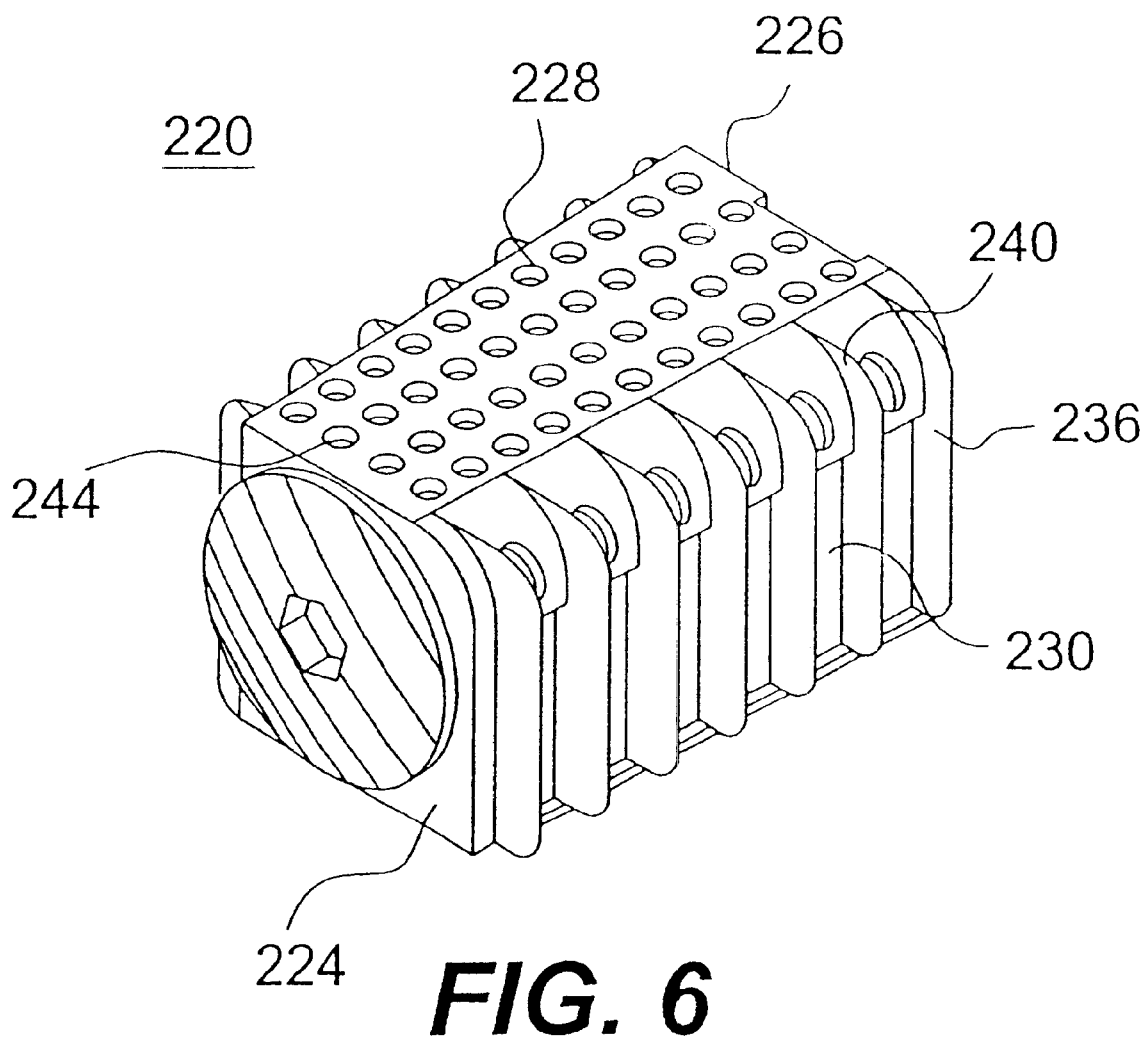
FIG. 6 is a perspective view of another embodiment of the spinal fusion implant of the present invention for posterior insertion oriented in an initial insertion position and configured for clockwise rotation within the disc space, the top and bottom walls thereof being tapered relative to one another for inducing angulation of the adjacent vertebral bodies.
Figure 7A:
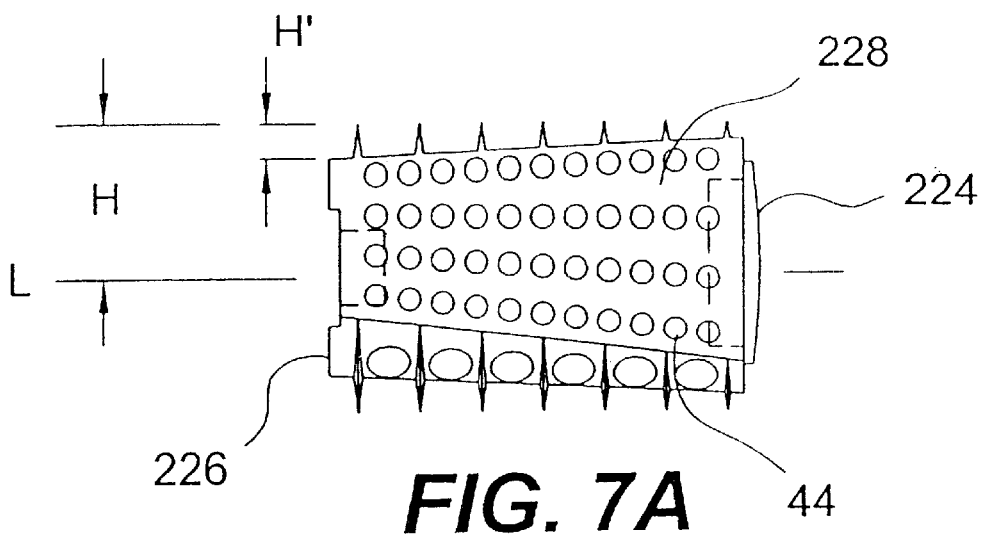
FIGS. 7A–7E are side, lower, upper, insertion end, and trailing end views, respectively, of the implant of FIG. 6 in a deployed orientation.
Figure 7B:
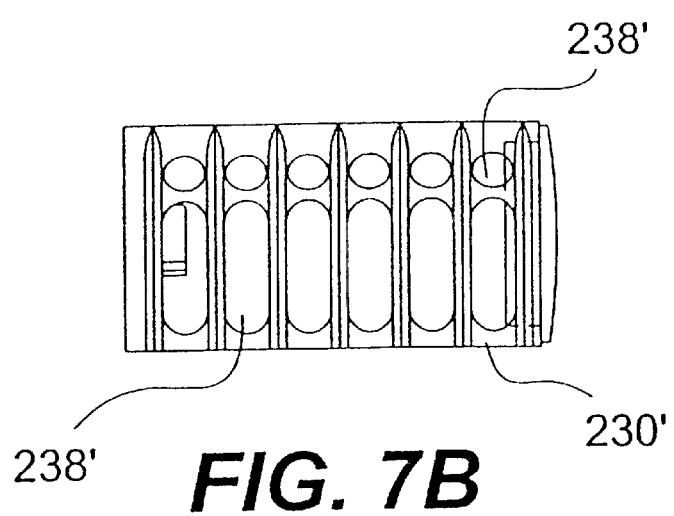
Figure 7C:
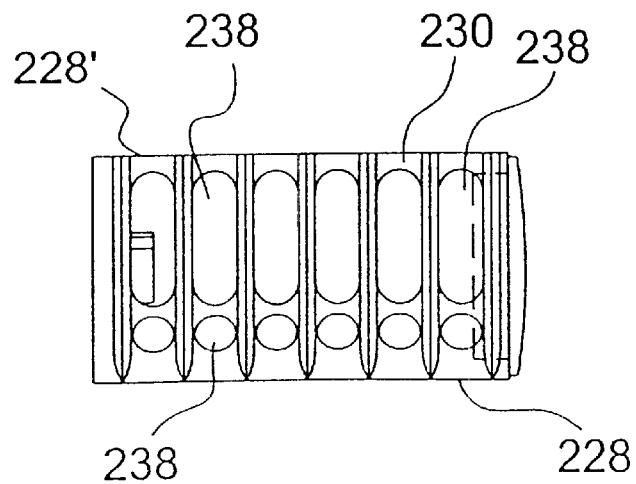
Figure 7D:
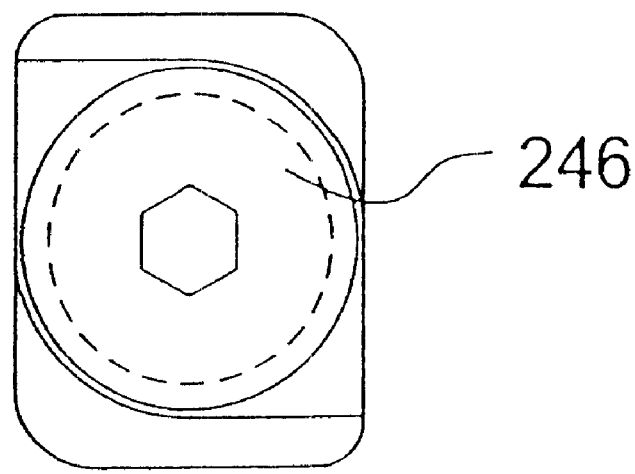
Figure 7E:
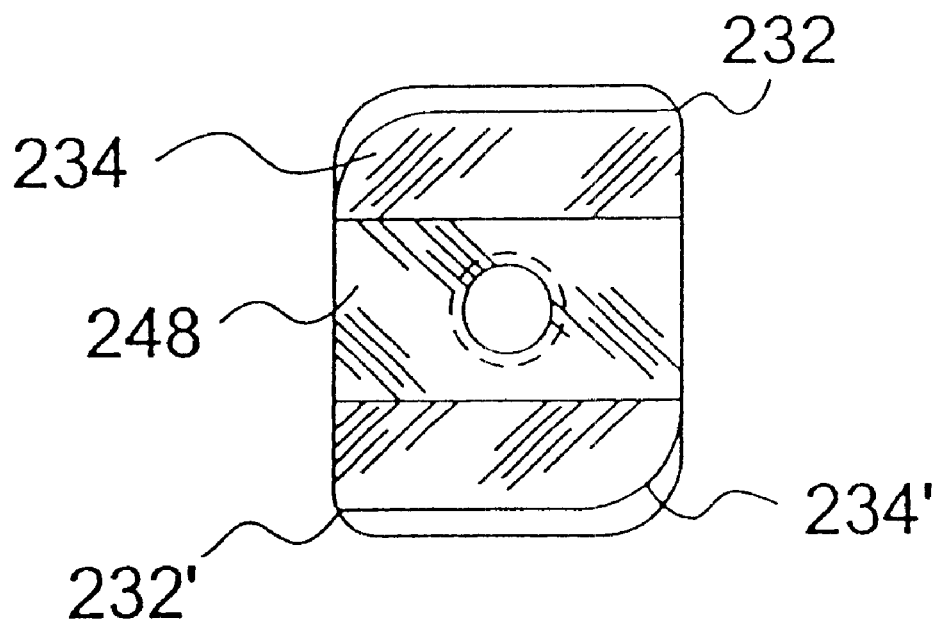
Figure 8:
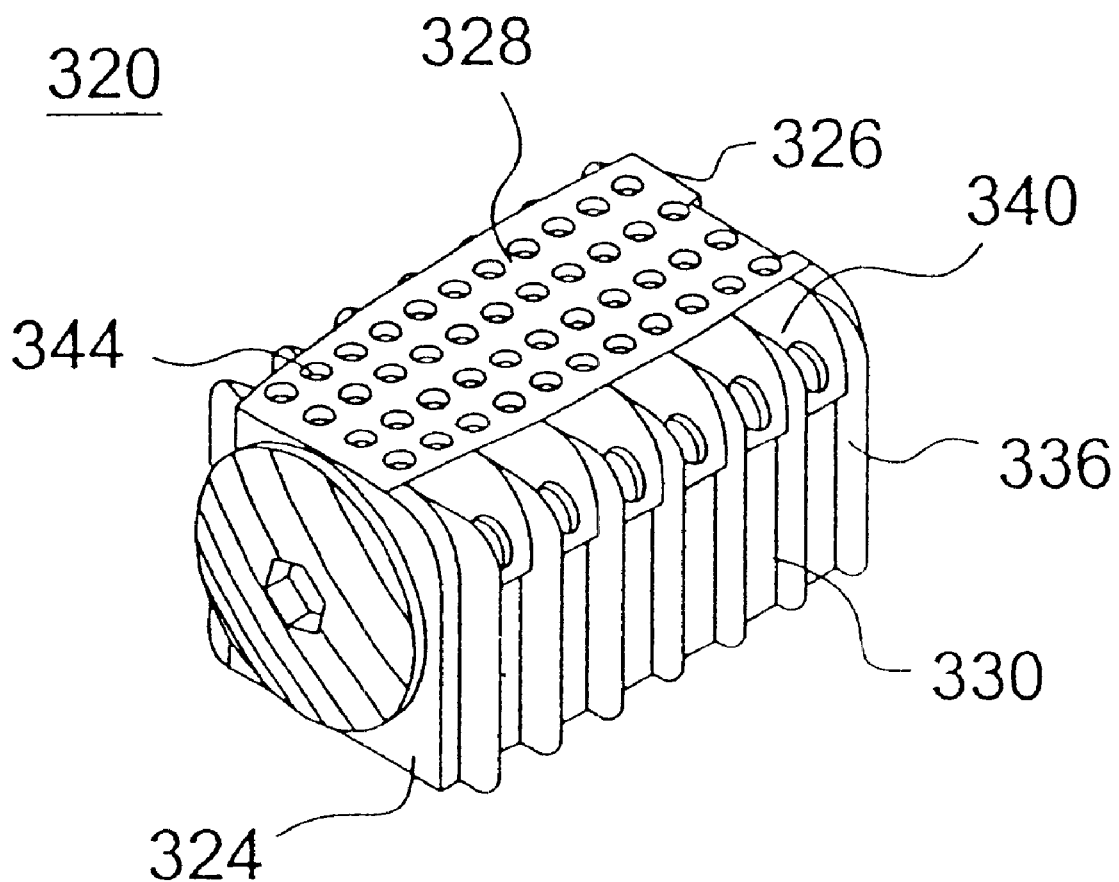
FIG. 8 is a perspective view of yet another embodiment of the spinal fusion implant of the present invention oriented in an initial insertion position and having anatomically shaped upper and lower walls configured to more generally conform to the natural contours of the endplates of the two adjacent vertebral bodies to be fused.
Figure 9A:
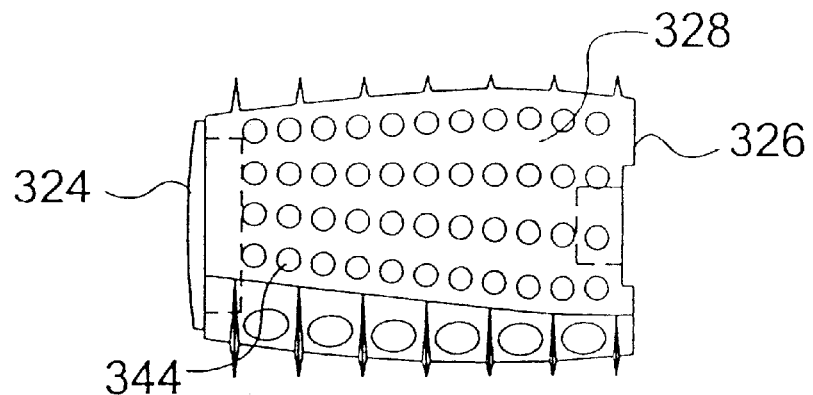
FIGS. 9A–9E are side, upper, lower, trailing end, and insertion end views, respectively, of the implant of FIG. 8 in a deployed orientation.
Figure 9B:
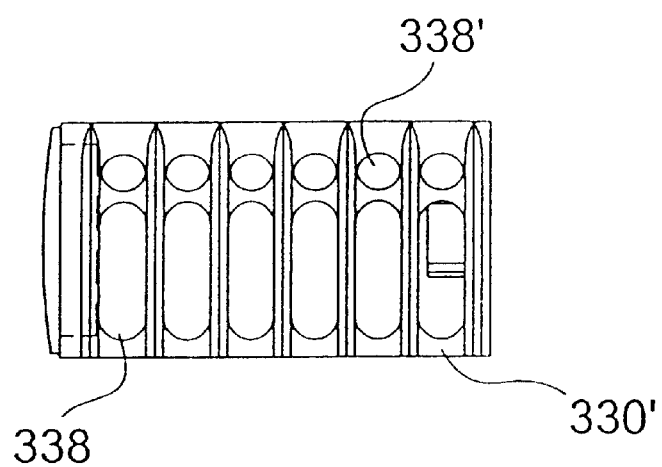
Figure 9C:
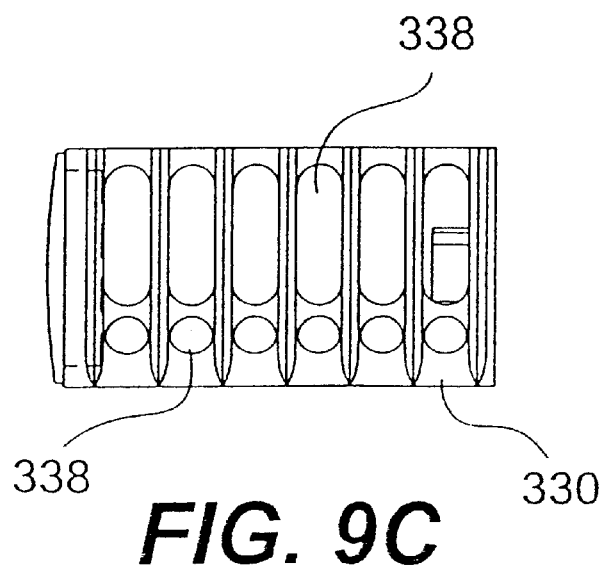
Figure 9D:
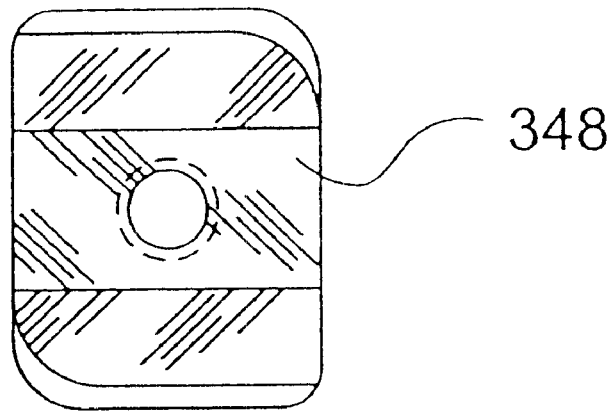
Figure 9E:
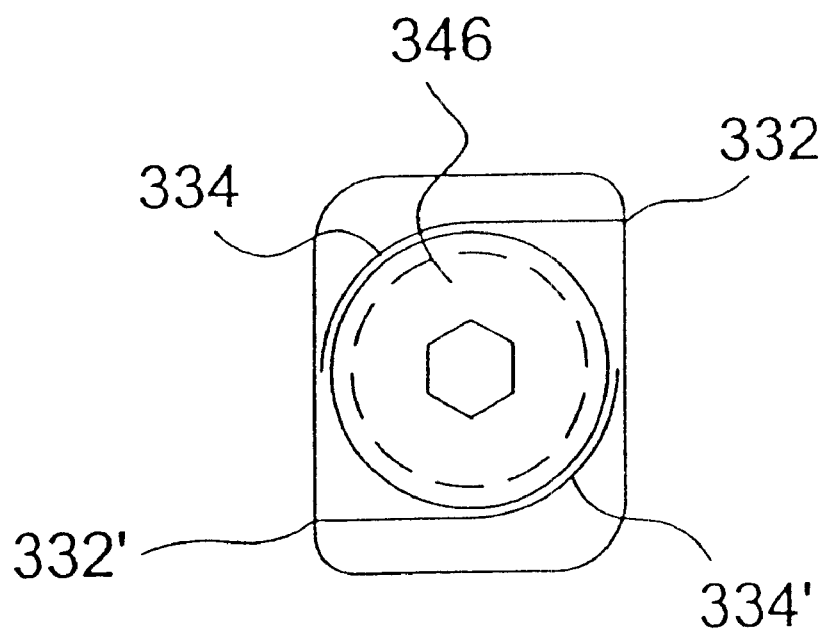
Figure 10:
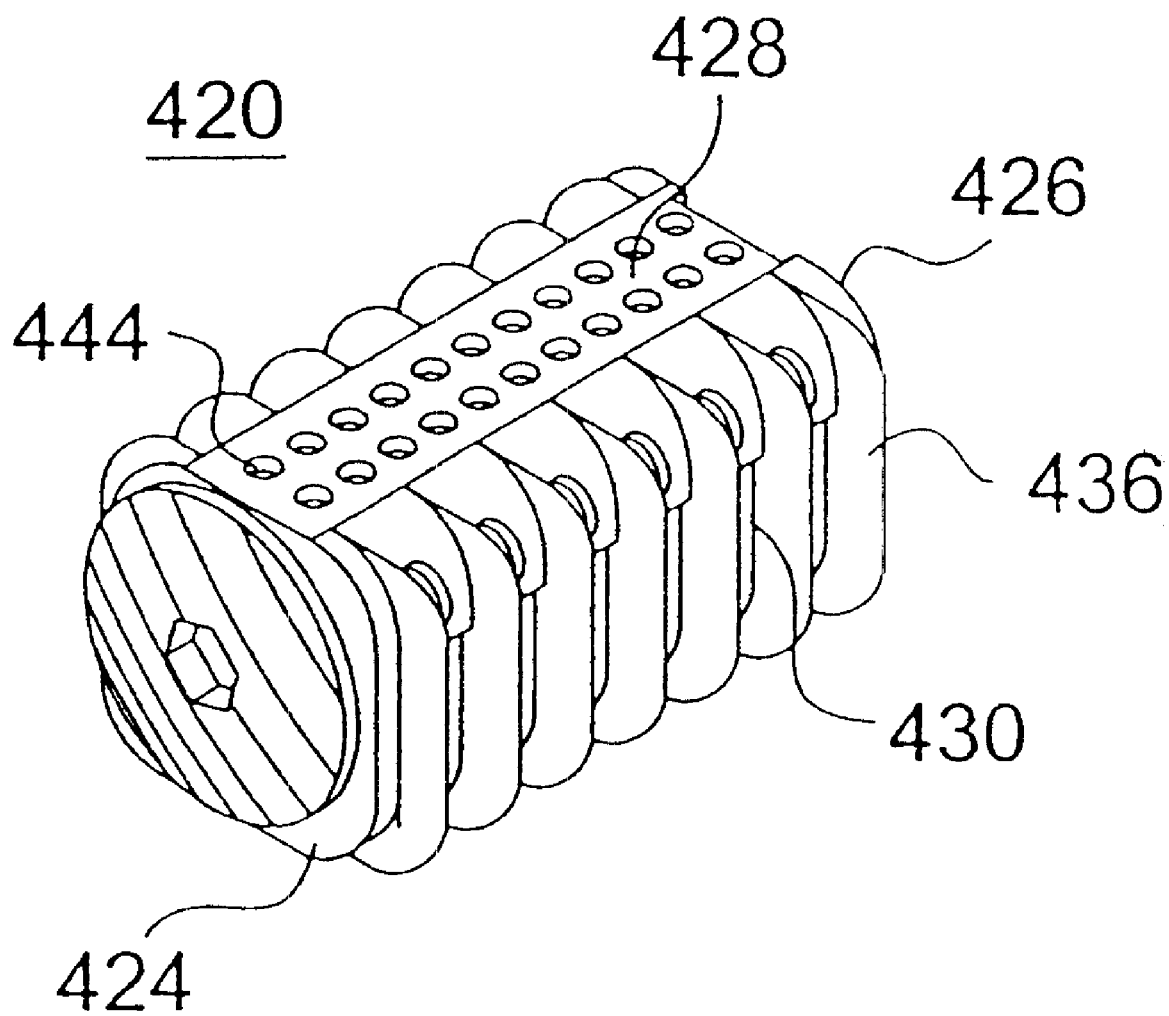
FIG. 10 is a perspective view of another embodiment of the spinal fusion implant of the present invention oriented in an initial insertion position and configured to be rotated in either direction within the disc space to a final deployed position.
Figure 11A:
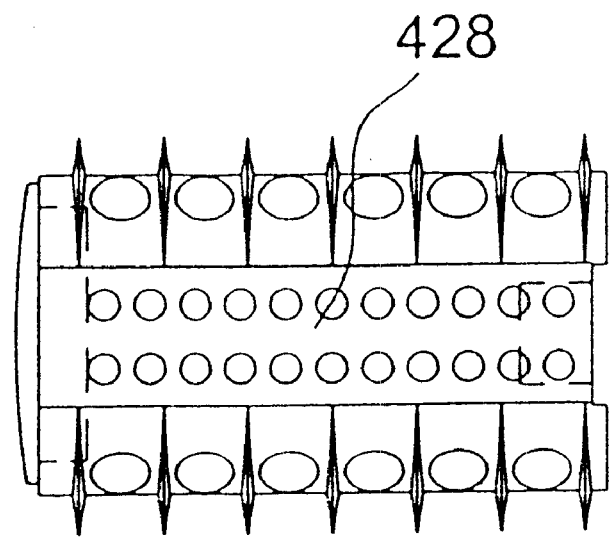
FIGS. 11A–11D are side, lower, trailing end, and insertion end views, respectively, of the implant of FIG. 10 in a deployed orientation.
Figure 11B:
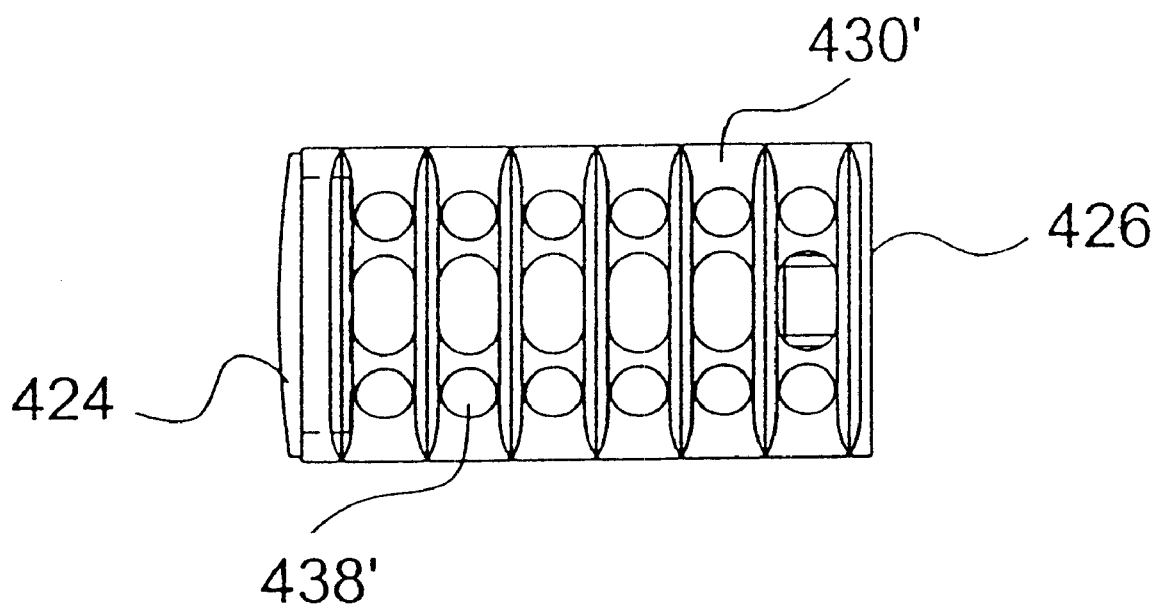
Figure 11C:
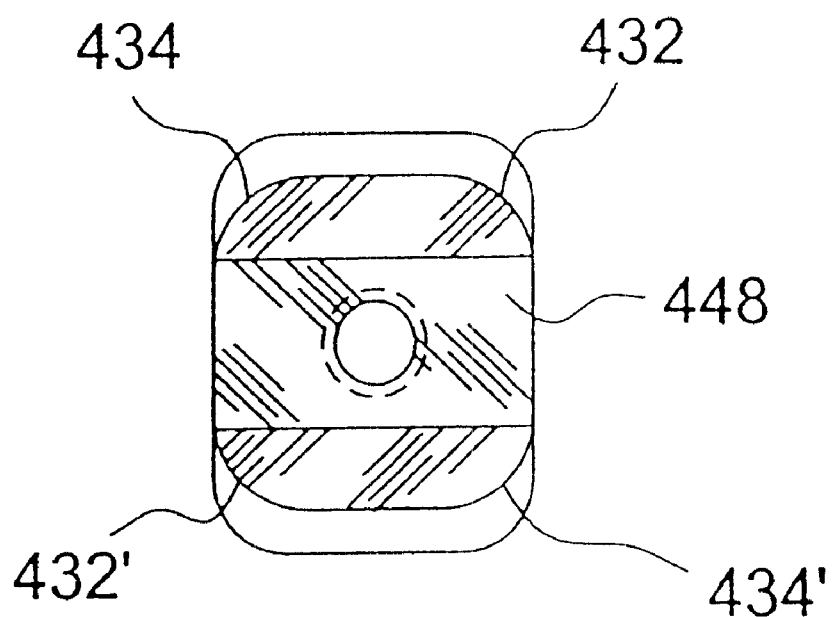
Figure 11D:
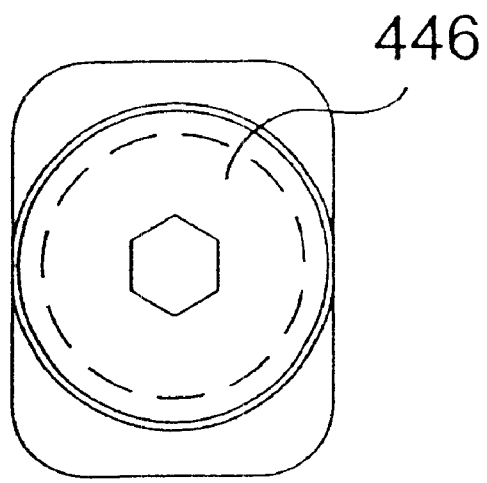

In accordance with another preferred embodiment of the present invention, and with further reference to FIGS. 4 and 5A–5E and with particular attention being drawn to FIG. 5A, the implant 120 includes upper and lower walls 130, 130' disposed in a diverging angular relationship to each other from insertion end 124 to trailing end 126 of body 122. This angular relationship preserves and/or restores lordosis in a segment of the lumbar or cervical spinal column when inserted from the anterior (front) aspect of the spine. Implant 120 of FIG. 4 has fins 136,136' having a substantially uniform height H measured from the central longitudinal axis L of implant 120 such that the overall height of fins 136,136' has an overall dimension that is substantially parallel to the longitudinal axis L. Fins 136,136' as measured from upper and lower walls 130, 130' have a height H' that varies along the length of implant 120. Alternatively, fins 136, 136' can have a height H measured from the longitudinal central axis L of implant 120 wherein the height H is variable along the length of implant 120.

In accordance with yet another preferred embodiment of the present invention, and with further reference to FIGS. 6 and 7A–7E, implant 220 includes upper and lower walls 230, 230' disposed in a converging angular relationship to each other from insertion end 224 to trailing end 226 of body 222. In this embodiment, when implant 220 is inserted from the posterior aspect of the spine, body 222 of implant 220 has a maximum height at a point nearest to insertion end 224 and a minimum height at a point nearest trailing end 226 so as to restore the natural lordosis of the spine at that spinal segment. This is facilitated by the fact that implant 220 is introduced in the disc space lying on its side, and the side to side dimension of body 222 is preferably uniform.

In accordance with yet another embodiment of the present invention, and with further reference to FIGS. 8 and 9A–9E, implant 320 includes upper and lower walls 330, 330' having a generally anatomical shape configured to substantially match the natural contours of the endplates of the adjacent vertebral bodies to be fused. This anatomical shape is best observed in FIGS. 8 and 9A wherein upper and lower walls 330, 330' are shown having a curvature oriented from insertion end 324 to trailing end 326. The generally anatomical shape may also include a contour of upper and lower walls 330, 330' from side to side of implant 320.

In accordance with yet another embodiment of the present invention, and with reference to FIGS. 10 and 11A–11D and FIGS. 12 and 13A–13D, implant 420 may comprise four diametrically opposed junctions that are radiused so as to permit rotation of the implant in both clockwise and counterclockwise directions. The specialized junctions of implant 420 need not be limited to portions of a circle. Alternatively, the junctions can be tapered, or in some other manner have a relief or cut out area to serve in a manner similar to the radiused areas previously described so that the reduced hypotenuse is substantially less than the other hypotenuse between the other diagonally, opposed junctions, which is an unreduced, an unmodified, or a theoretical hypotenuse or at least a hypotenuse reduced to a lesser extent than the reduced hypotenuse, and thus the reduced hypotenuse is closer in height to the body of the implant.

Figure 12:
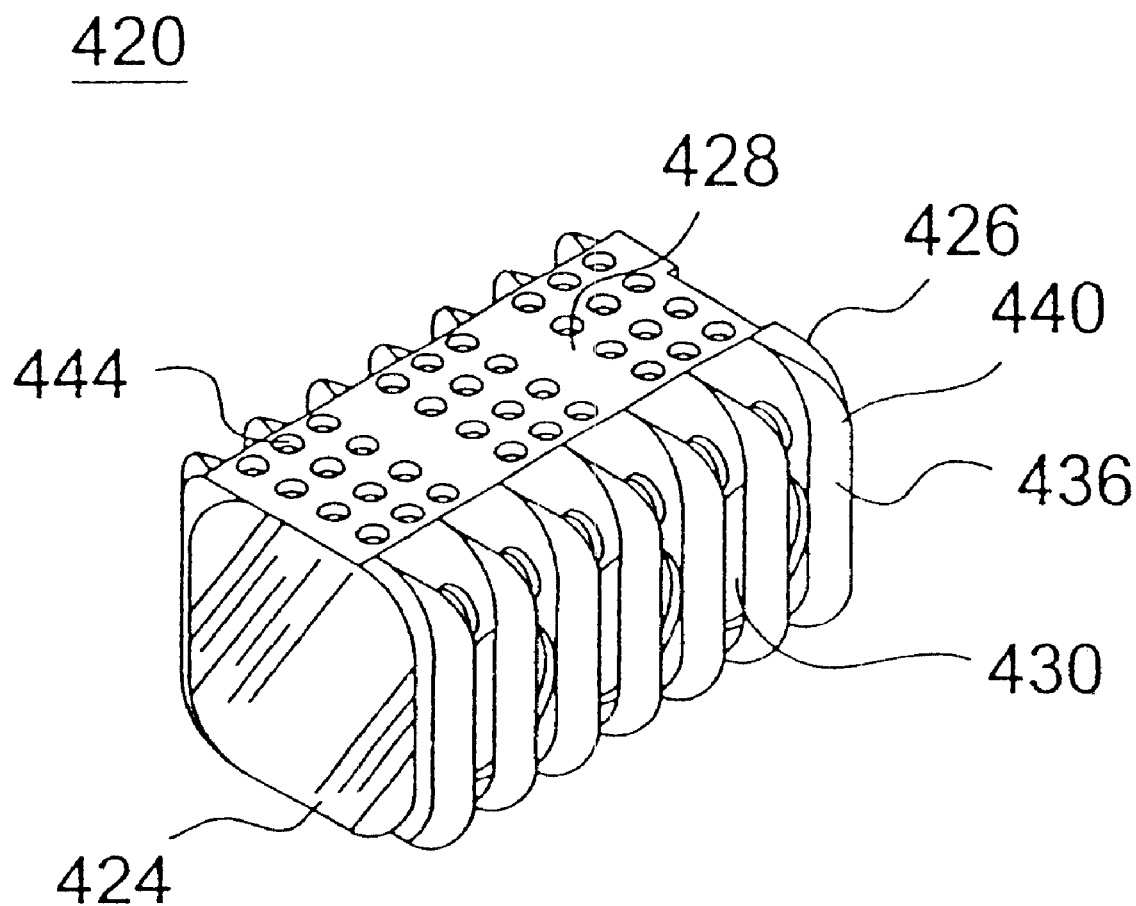
FIG. 12 is a perspective view of another spinal fusion implant made in accordance with the present invention oriented in an initial insertion position and configured for rotation in either direction within the disc space to a final deployed position.
Figure 13A:
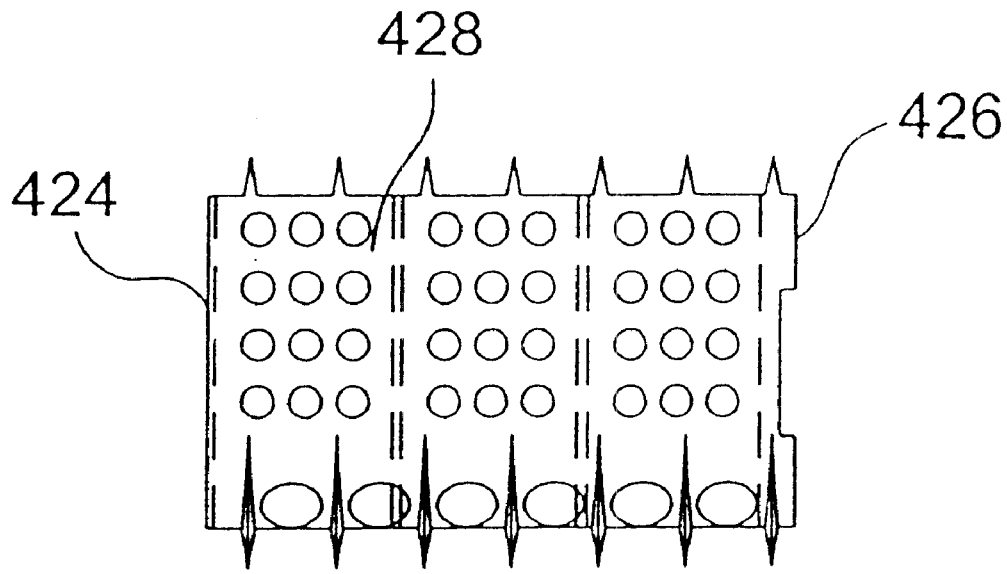
FIGS. 13A–13D are side, lower, trailing end, and insertion end views, respectively, of the implant of FIG. 12 in a deployed orientation.
Figure 13B:
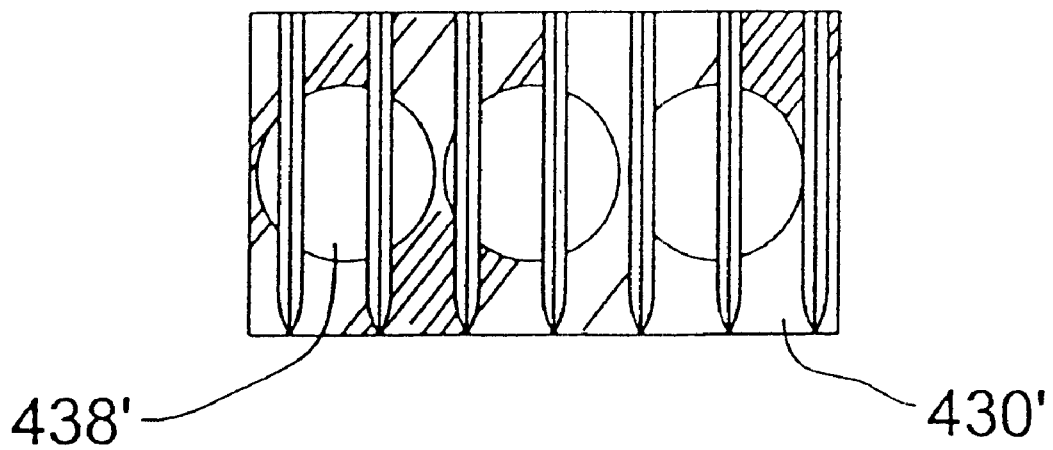
Figure 13C:
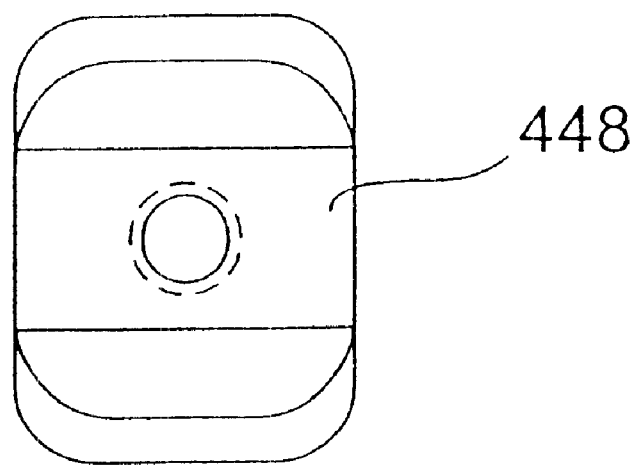
Figure 13D:
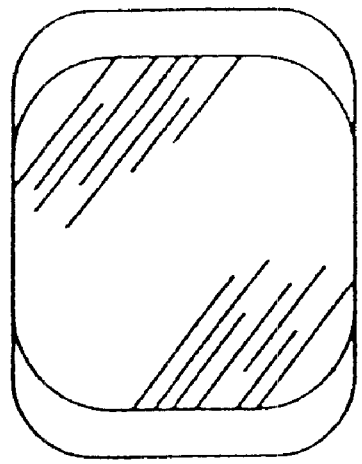
Figure 14:
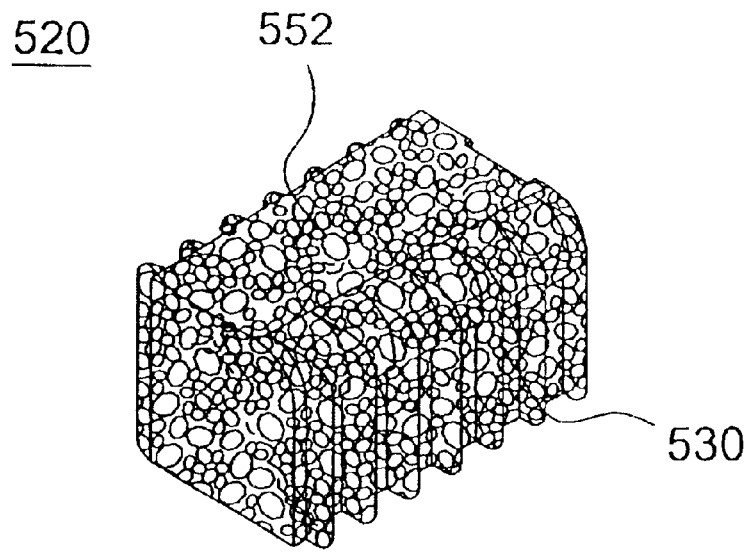
FIG. 14 is a perspective view of yet another spinal fusion implant of the present invention oriented in an initial insertion position and made of a porous material.
Figure 15A:
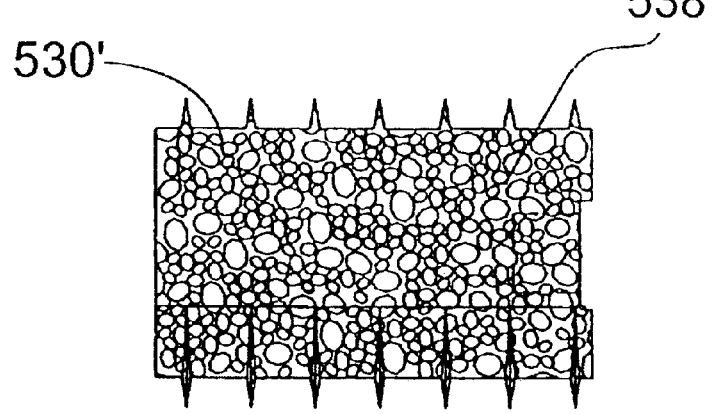
FIGS. 15A–15D are side, upper, trailing end, and insertion end views, respectively, of the implant of FIG. 14 in a deployed orientation.
Figure 15B:
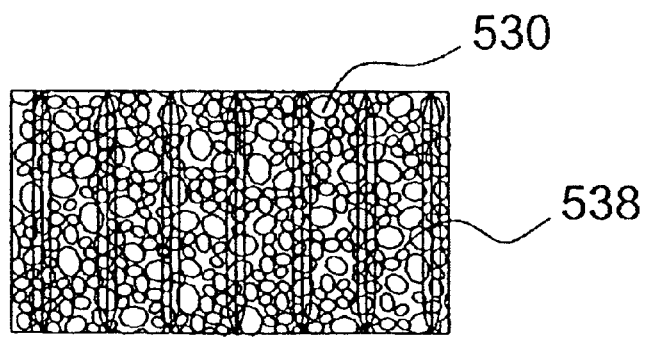
Figure 15C:
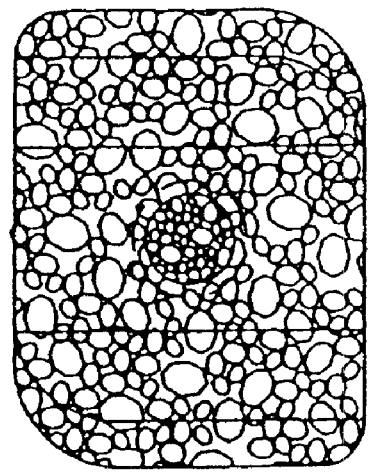
Figure 15D:
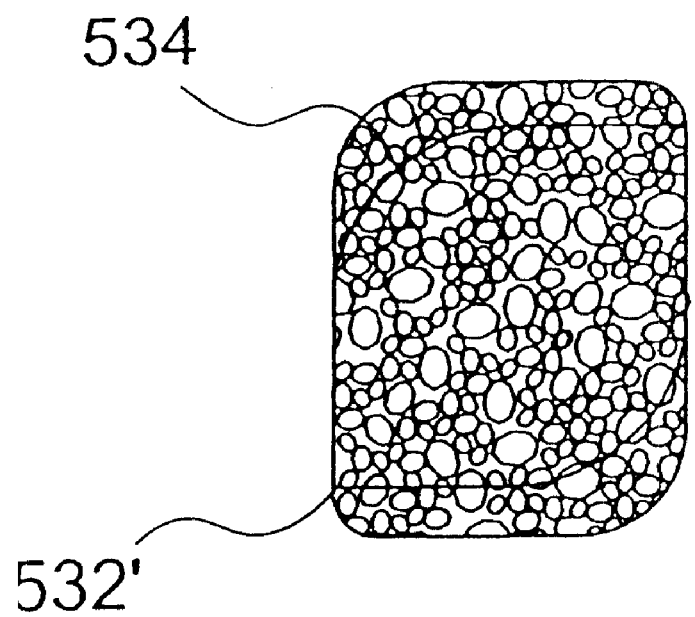

Implant 420 of FIGS. 12 and 13B shows use of three large openings 438 passing through upper wall 430, into the implant, and through openings 438' in lower wall 430'. These openings allow for the growth of bone in continuity from adjacent vertebral body to adjacent vertebral body through implant 420. It is understood that upper and lower walls 430, 430' can have fewer than or more than the number of openings 438, 438' herein shown. Such an alternative embodiment readily lends itself to being loaded with osteogenic material such as bone without resort to an end opening to the implant which is not an essential feature of the implant.

In accordance with yet another preferred embodiment of the present invention, and with further reference to FIGS.14 and 15A–15D, implant 520 comprises a porous material with a plurality of openings 538, 538' within a surface and generally being 1.0 mm or less in diameter. Openings 538, 538' are the ends of channelings passing entirely through implant 520 such that there are passageways from upper wall 530 to lower wall 530' to allow the growth of bone from vertebral bodies to vertebral bodies through the implant. Because of its porous nature, implant 520 is able to hold fusion promoting materials and further provides for an increased surface area of contact and engagement when opposed to the adjacent vertebral bodies. By increasing both surface area and contact, implant 520 further promotes the process of interbody fusion. In this particular implant at least a significant portion of the pores of the outer surface 552 are in the range of 50–500 microns with a significant portion of those in the range of 250–500 microns in diameter. Because of its porous nature, implant 520 also lends itself well to being coated with bioactive fusion promoting substances such as bone morphogenetic proteins or genetic material to induce bone formation in the recipient. Such materials include sequences of nucleic acids comprised of cytosine guanine adenine thymine (CGAT). While implant 520 in FIGS. 14 and 15A–15D are shown as being solid, it should be appreciated that implant 520 can be made to be substantially hollow or hollow in part.

Figure 16A:
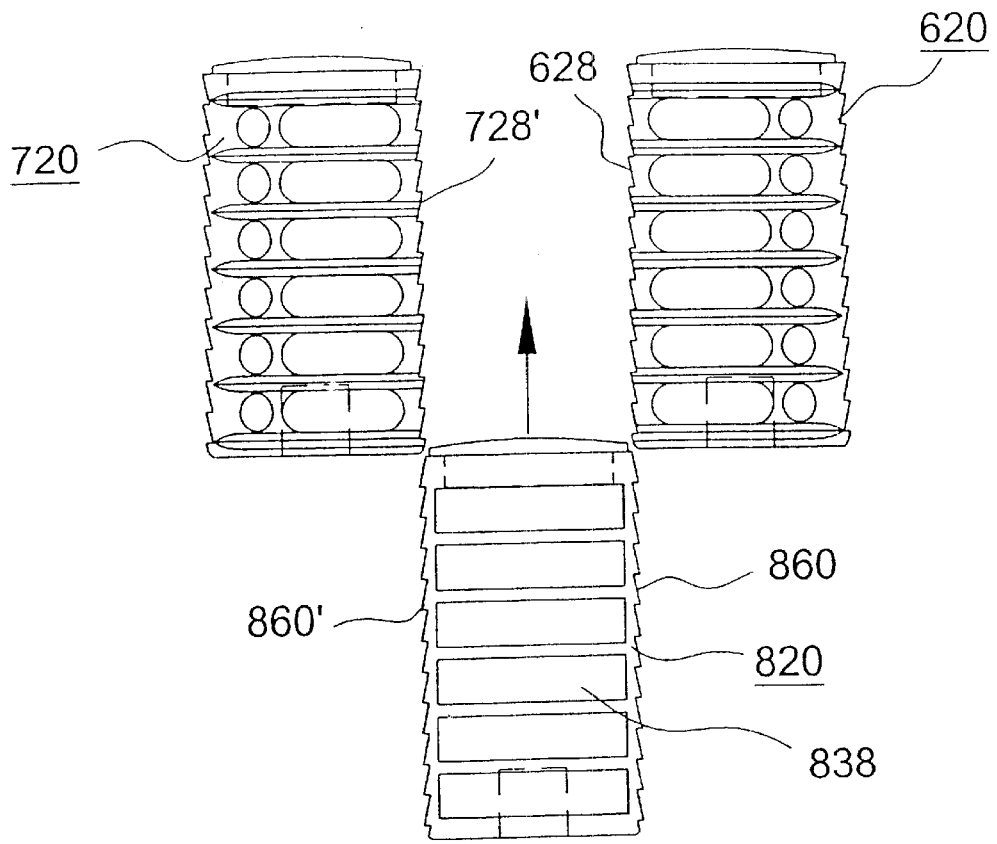
Figure 16B:
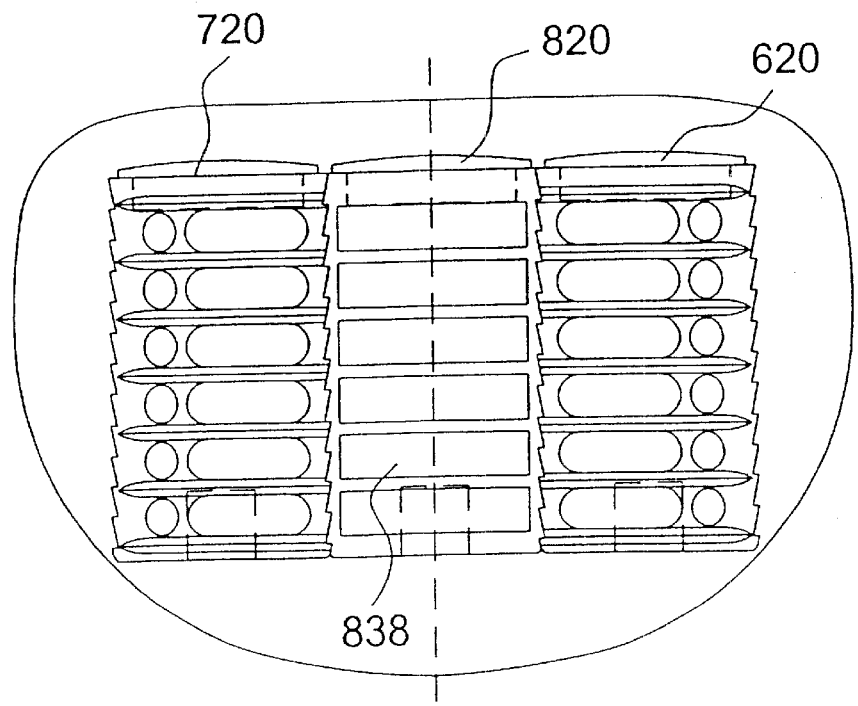
FIG. 16B is a top view of the implants of FIG. 16A with the third implant deployed between the clockwise rotation and counter-clockwise rotation implants within a disc space.
Figure 16C:
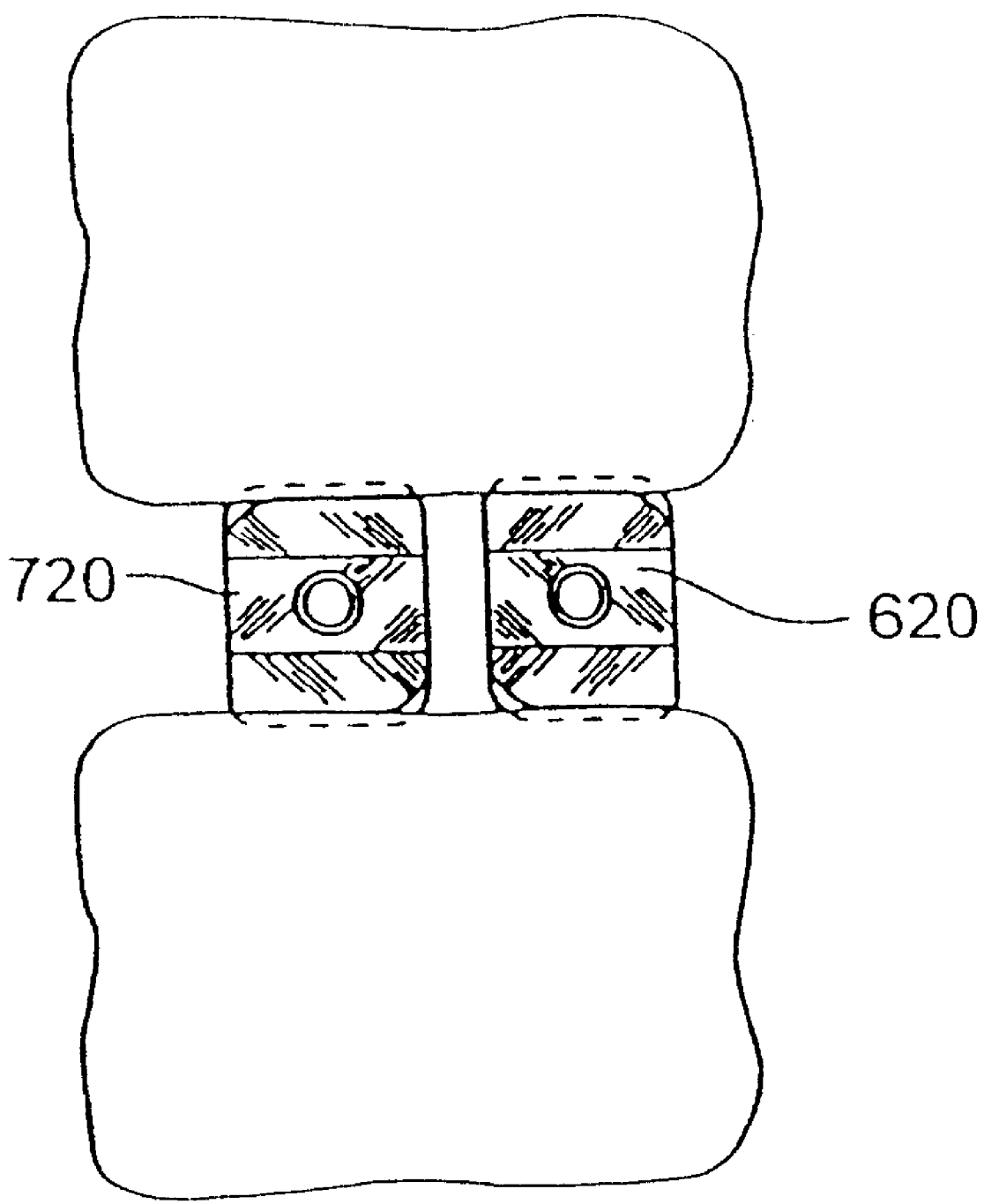
FIG. 16C is a trailing end view of the clockwise and counter-clockwise rotation spinal fusion implants of FIGS. 16A and 16B deployed between adjacent vertebral bodies.
Figure 17:
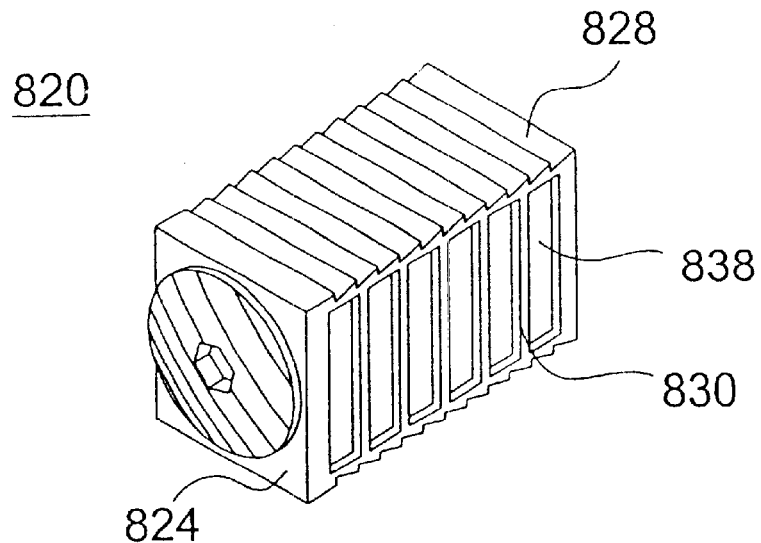
FIG. 17 is a perspective view of a preferred embodiment of the third implant of FIGS. 16A and 16B in accordance with the present invention lying on its side.

FIGS. 16A and 16B show an alternative embodiment of the present invention that has previously been referred to as third implant 820 or the middle implant. This third implant is for use between first implant 620 and second implant 720 in accordance with the embodiments described above. Within the preferred embodiment of the implant set, first implant 620 is configured to rotate, by preference only, in a first direction while second implant 720 is configured, again as a matter of preference only to rotate in a second direction opposite the first direction. Each of first and second implants 620, 720 rotate from a more central to a more lateral position. Thus, as best shown in FIG. 16C, in this embodiment, first implant 620 rotates clockwise while second implant 720 rotates counterclockwise. Third implant 820 is configured for placement between first and second implants 620, 720 and has contacting surfaces 860, 860' for contacting the adjacent side walls 628, 728' of first and second implants 620, 720, respectively.

Figure 18A:
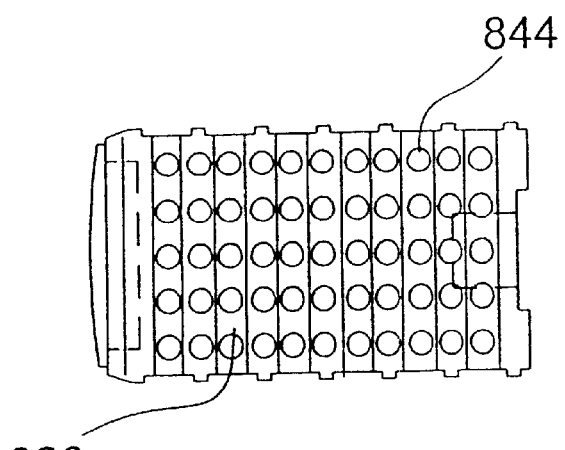
FIGS. 18A–18D are side, upper, trailing end, and insertion end views, respectively, of the implant of FIG. 17 in a deployed orientation.
Figure 18B:
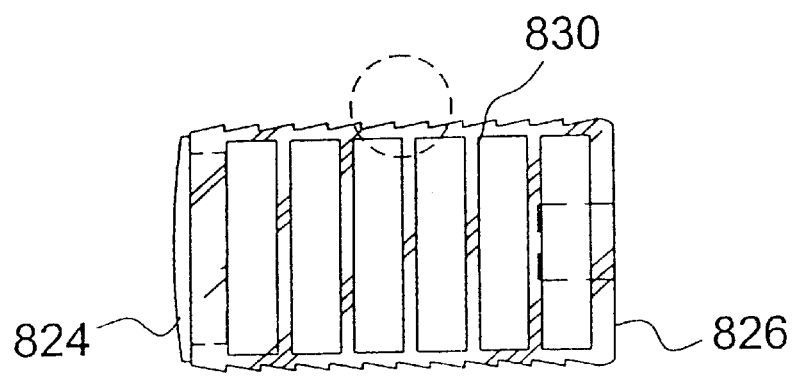
Figure 18C:
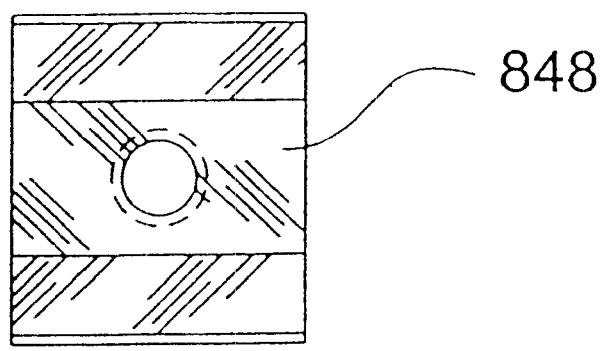
Figure 18D:
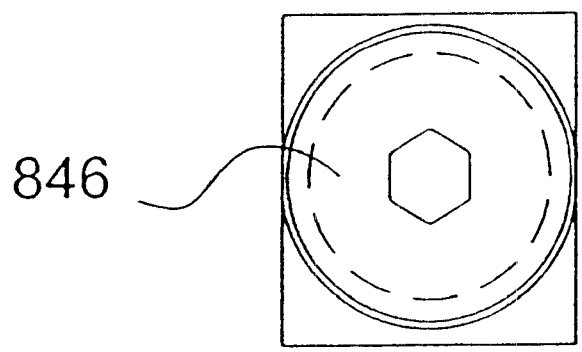
Figure 18E:
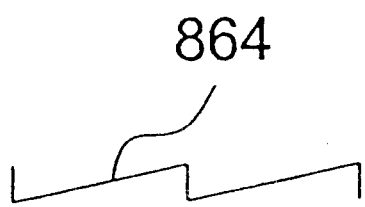
FIG. 18E is an enlarged fragmentary sectional view of a cooperating side surface of the implant of FIG. 18B.
Figure 19A:
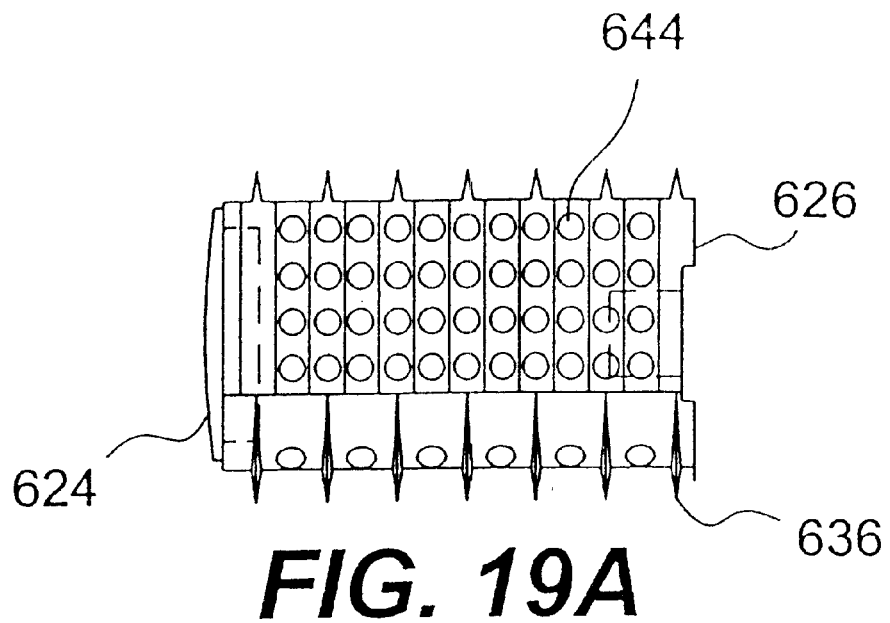
FIGS. 19A and 19B are side and upper views, respectively, of a spinal implant made in accordance with an embodiment of the present invention having a cooperating surface for engaging the cooperating surface of the third implant shown in FIGS. 17, 18A, 18B, and 18E.
Figure 19B:
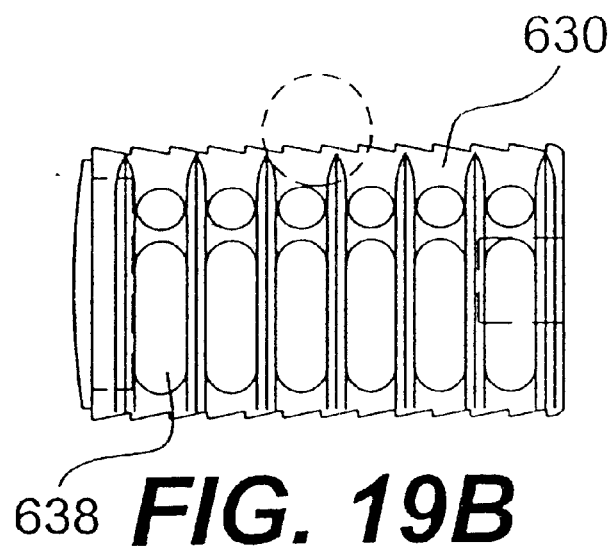
Figure 19C:
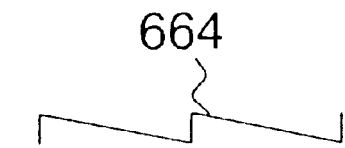
FIG. 19C is an enlarged fragmentary sectional view of the cooperating surface of the implant of FIG. 19B.

As best seen in FIGS. 17 and 18A–18D, third or middle implant 820 has openings 838 for permitting bone growth from vertebral body to vertebral body and preferably openings 844 in the side walls 828 of the implant 820 to allow for the growth of vascularity and bone through implant 820 and adjacent implants 620 and 720. Implant 820 is not configured to facilitate rotation since it is inserted into the spine already correctly oriented with upper and lower walls 830, 830' to contact the adjacent vertebral bodies. Upper wall 830 and lower wall 830' preferably include ridges 864 or other surface projections for engaging the adjacent vertebral bodies. Side walls 828, implant 820 include surface projections for engaging complementary surface projections on the side walls 628, 728' of implants 620 and 720, respectively. The present embodiment preferably includes ridges 860 formed of forward facing ratchetings that permit implant 820 to be easily slid between implants 620 and 720 but resists its dislodgement in a direction counter to its insertion. It can be seen in FIGS. 16B and 18E how the forward facing side wall ratcheting of implant 820 cooperate with the reversed side wall ratchetings of implants 620 and 720 to bind the three implants together side by side.

Figure 20A:
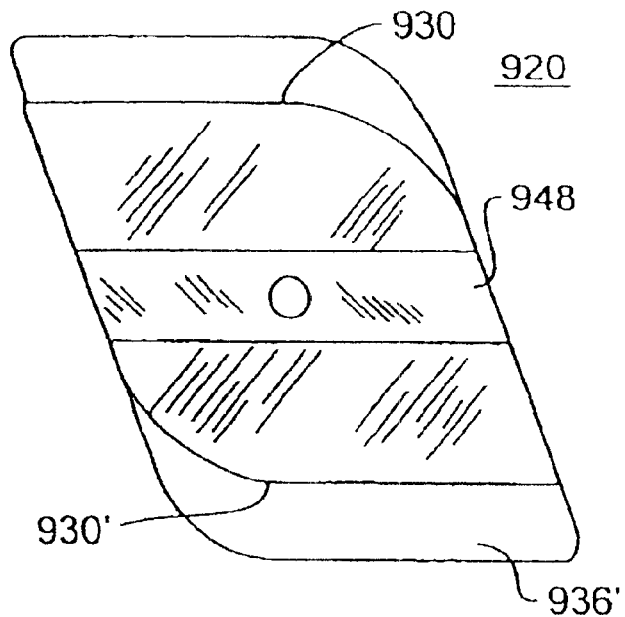
FIGS. 20A and 20B are trailing end and insertion end views, respectively, of an to alternative embodiment of a spinal fusion implant of the present invention.
Figure 20B:
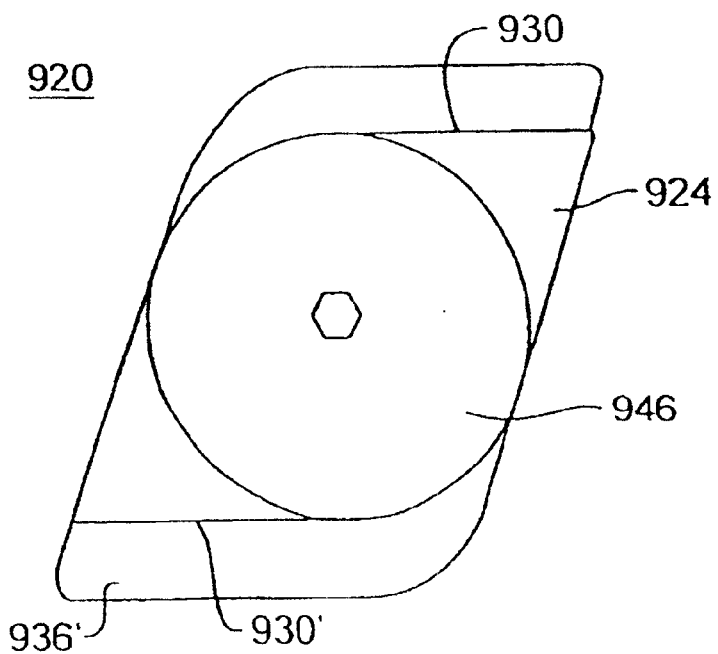

In accordance with yet another preferred embodiment of the present invention, and with further reference to FIGS. 20A and 20B, implant 920 is configured to rotate less than 90 degrees from an initial insertion position to a final, deployed position. This embodiment of the present invention preferably has a rotation of approximately 70 degrees. An implant configured for less than 90 degrees of rotation can have larger contact areas for upper and lower walls 930 and 930' than a comparable height 90 degree rotation implant.

Figure 21:
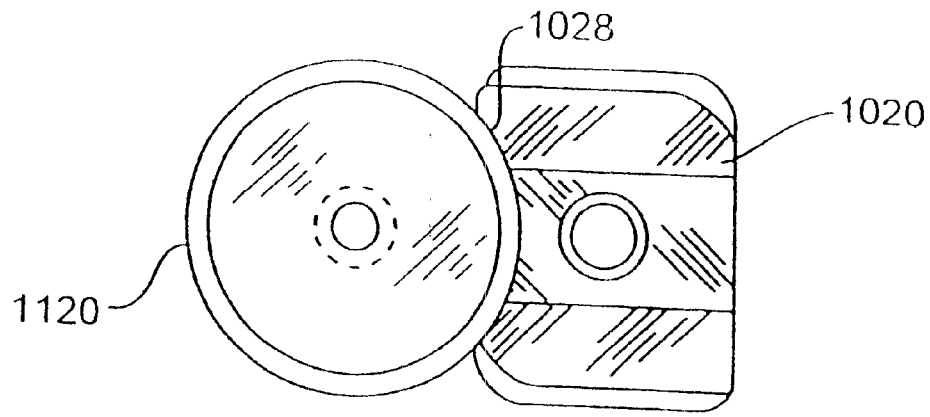
FIG. 21 is a trailing end view of yet another embodiment of a spinal fusion implant of the present invention configured to cooperatively receive an adjacent implant.
Figure 22:
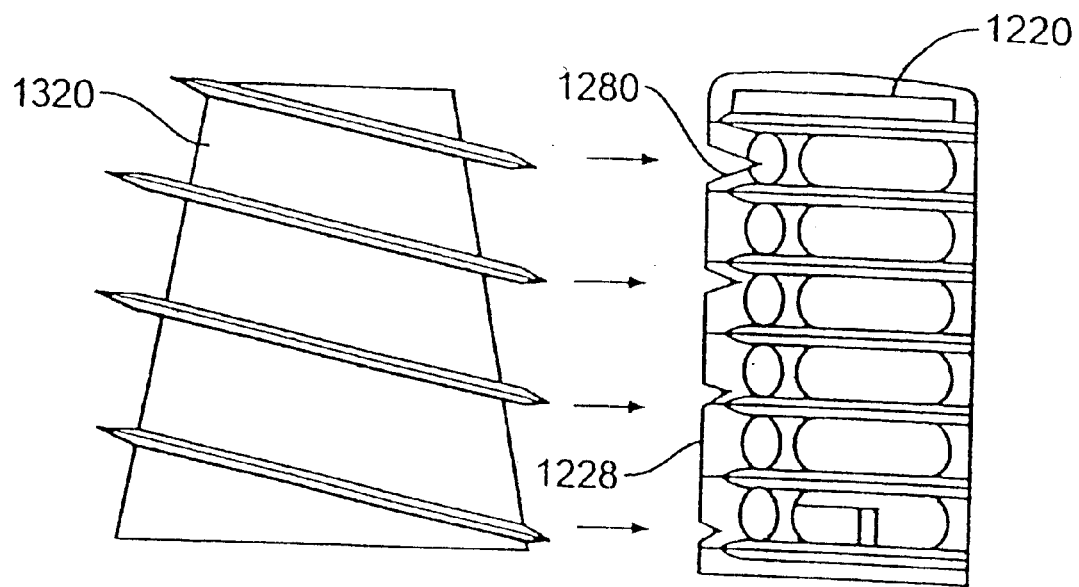
FIG. 22 is a top view of another embodiment of a spinal fusion implant of the present invention configured to cooperatively receive an adjacent implant.

In accordance with another preferred embodiment of the present invention, and with further reference to FIG. 21, implant 1020 has at least one side wall 1028 that is configured to mate with another implant 1120. In particular, FIG. 21 illustrates a trailing end view of an embodiment of the present invention having a concave side wall 1028 to cooperatively mate with either of a cylindrical, partial cylindrical, tapered, threaded or push-in interbody implant 1120. Sidewall 1028 may be concave or be incomplete providing an opening to accommodate implant 1120 or otherwise relieved to allow for implants 1020 and 1120 together to have a width less than the sum of their maximum widths apart. Alternatively, yet another embodiment of the present invention is shown in FIG. 22, and includes an implant 1220 having grooves 1280 in at least one side wall 1228 for cooperatively receiving threads from an adjacent threaded interbody implant 1320. While implant 1320 is of a tapered design it could be more or less cylindrical and its surface projections could be other than a thread. Also, implant 1220 may have an incomplete sidewall 1228 with openings therein to accommodate the projections or thread of implant 1320.

Having described certain preferred embodiments of the implant of the present invention, the method for deploying this implant will now be described in more detail. The method comprises the steps of: removing at least a portion of the disc from between the adjacent vertebral bodies so as to at least in part expose the vertebral endplates of those adjacent vertebral bodies; providing a first implant having an insertion end, a trailing end, side walls, upper and lower walls, and protrusions, which protrusions are preferably but not necessarily in the form of fins extending outwardly from the opposed upper and lower walls. Preferably, the upper and lower walls have at least one, or alternatively a plurality of openings passing therethrough so as to allow for the growth of bone in continuity from one of the adjacent vertebral bodies to the other of the adjacent vertebral bodies through the spinal fusion implant. The implant includes a cross-section with the side walls intersecting the upper and lower walls at opposed junctions, two of which are preferably diametrically opposed arcuate portions. The method also includes the steps of inserting the first implant by linearly advancing it between the adjacent vertebral bodies with the side walls facing the endplates of the adjacent vertebral bodies, and then rotating the first implant 90 degrees into a deployed position such that the fins penetrate the endplates of the adjacent vertebral bodies. When the implant is deployed, the upper and lower walls from which the fins extend will then be placed into contact and support through the endplate regions of the adjacent vertebral bodies the vertebral endplates themselves.

The inserting step may include positioning the adjacent vertebral bodies in relative angular position to each other by the step of rotating the implant 90 degrees about its longitudinal axis. The method may further comprise of the step of loading the first implant with osteogenic material prior to insertion of the implant. The method may further comprise compressibly loading fusion promoting materials within the interior of the implant prior to its insertion. The rotating step may further include the sub-step of initiating rotation in a direction so that the two diametrically opposed arcs of radii rotate toward the nearest of the adjacent vertebral bodies respectively. Additionally, the rotating step may include the sub-step of rotating the first implant from its position after the insertion step to a deployed position without substantial additional distraction of the adjacent vertebral bodies.

The method may further comprise of the step of attaching a driver to the first implant, the preferred driver being capable of both pushing and pulling the implant while rotating the implant both clockwise and counterclockwise. The method may further comprise using the driver to insert the implant through a guard either with or without disc penetrating extensions or in combination with a distractor as disclosed in U.S. Pat. Nos. 5,484,437 and 5,797,909, which are hereby incorporated by reference.

The method may further comprise the steps of providing a second implant having an insertion end, a trailing end, side walls, upper and lower walls, and fins extending outwardly from the upper and lower walls. The upper and lower walls preferably have openings which pass therethrough that are configured to allow for the growth of bone therethrough and from vertebral body to vertebral body through the implant. The second implant has a cross-section with the side walls intersecting the upper and lower walls at junctions, two of which are preferably diametrically opposed arcuate portions. The second implant is inserted between the adjacent vertebral bodies with the side walls directed toward the adjacent vertebral bodies and then rotated 90 degrees into a deployed position such that the upper and lower walls then contact and support each of the adjacent vertebral endplate regions while the fins extending from the upper and lower walls are then penetrably driven through the vertebral endplates. The implant is rotated to drive the fins into the substance of the vertebral bodies.

As a substep of that method, the first implant may be deployed by rotating it 90 degrees in a first direction while the second implant may be deployed by rotating it in either the same direction or in the opposite direction.

The method may further comprise of lateralizing (moving lateral) the first and second implant to provide a space between the first and second implants. The method may still further comprise placing within that space a third specialized implant different in structure from the first and second implants in that while it is designed to be inserted by linear advancement, it is not designed to be rotated into place. Further, the specialized third implant preferably includes protrusions or ratchetings on its outer walls so as to engage the implant to the adjacent vertebral bodies and to the first and second implants. This specialized third implant preferably has upper and lower walls for contacting each of the adjacent vertebral bodies. The upper and lower walls preferably have at least one opening to allow for the growth of bone in continuity from a first adjacent vertebral body through the implant to the second adjacent vertebral body. A third implant preferably is inserted between the first and second implant and between the adjacent vertebral bodies with opposed upper and lower walls directed towards the adjacent vertebral bodies. The step of inserting the third implant may include a substep of contacting the first and seconds implants with the side walls of the third implant and a substep of securing the third implant to the first and second implants. The securing substep preferably includes a substep of providing the first, second, and third implants with cooperating engaging surfaces along the side walls of each implant at least where the implants are in contact with one another.

When the implants are rotated approximately 90 degrees, while they do not cause an over distraction of the inner space, they nevertheless create a path through the adjacent vertebral endplates of the fins that may be approximately one and a half times the width of the implant itself. When a first, second, and third implants are inserted into the disc space, the first and second implants migrate as described above, approximately 50 percent of their width laterally to create room for the third implant with a width the same as the first and second implants. The third implant uses the 50 percent extra area cut by of each of the first and second implants. The track that is cut in each of the adjacent vertebral bodies by the fins of the first and second implants acts as a pathway of less resistance to allow these implants to slide laterally. A third implant with a width greater than or lesser than that of said first and second implants may also be utilized without departing from the scope of the present invention.

The method for inserting these implants may also include use of a cutting tool patterned like the implant but made of a material either stronger than or sharper than the implant. For example, if the implant were made of a carbon fiber or resorbable plastic, or bone, it may be desirable to utilize a cutting tool such as a rotary broach to cut the path that the fins of the implant would than occupy but not use the fins of the implant to do the actual cutting work.

The method may further include the step of scrapping or otherwise working upon the endplates until at least partially decorticated, i.e. worked upon to access the vascularity deep to the outer most aspect of the endplates itself prior to the step of inserting the implant. The step of removing may include the step of exposing the endplates of the adjacent vertebral bodies by removing sufficient disc material including both annulus fibrosus and nucleus pulposus from between the adjacent vertebral bodies. The providing step may include providing the first implant with at least one of the leading end and the trailing end of the body with an opening in communication with a hollow portion and adapted to cooperatively engage a cap. The providing step may also include providing the first implant in combination with a removable cap for closing the opening in at least one of the leading end and the trailing end of the body. The method may further include the step of loading or compressively loading the implant with osteogenic material.

The inserting step includes the sub-step of linearly advancing the implant between the adjacent vertebral bodies. The linearly advancing step includes the sub-steps of pushing the implant between the adjacent vertebral bodies or driving the implant between the adjacent vertebral bodies with percussion. The method may further include the step of distracting the adjacent vertebral bodies sufficiently for insertion of the implant prior to the inserting step. The method may further include the step of retracting the dural sac on the posterior side the adjacent vertebral bodies prior to the inserting steps. The step of inserting the implant may occur from an anterior aspect of the spine in which case the great blood vessels on the anterior side the adjacent vertebral bodies are retracted prior to the inserting step. The method may further include the step of inserting a rotary broach between the adjacent vertebral bodies, the broach having opposed sides for sliding against the adjacent vertebral bodies and a cutting portion for broaching into each of the adjacent vertebral bodies transverse to the long axis of said broach. The step of rotating includes rotating the broach so as to the drive cutting elements along the length of cutting portion of the broach into each of the adjacent vertebral bodies transverse to the long axis of the broach.

Other embodiments of the invention will be apparent to those skilled in the art from consideration of the specification of the invention disclosed herein. It is intended that the specification and examples may be considered as exemplary only, and the true scope and spirit of the invention be indicated by the following claims.

What I claim is:

1. An interbody spinal fusion implant for insertion across a disc space between adjacent vertebral bodies of a human spine, the implant comprising:

a body having an insertion end, a trailing end, an upper wall, a lower wall, and opposed side walls, said body having a cross-section with a height measured between said upper and lower walls and a width measured between said side walls, said side walls intersecting said upper and lower walls at four junctions, a first pair of diagonally opposed junctions having a distance therebetween substantially the same as the height of said body, a second pair of diagonally opposed junctions having a distance therebetween greater than the distance between said first pair of diagonally opposed junctions; and fins extending outwardly from said opposed upper and lower walls adapted to penetrate and extend within the vertebral endplates of the adjacent vertebral bodies upon rotation of the implant approximately 90 degrees from an initial insertion position to a final deployed position.

2. The implant of claim 1, wherein said side walls have a distance therebetween adapted to contact the adjacent vertebral bodies upon initial insertion of said implant into the spine.

3. The implant of claim 1, wherein each of said side walls are planar.

4. The implant of claim 3, wherein said side walls are generally parallel to one another.

5. The implant of claim 1, wherein the shape of each of said side walls is substantially a parallelogram.

6. The implant of claim 1, wherein said upper and lower walls have a distance therebetween adapted to support the vertebral endplates of the adjacent vertebral bodies upon rotation of said implant from an initial insertion position to a deployed position in the disc space.

7. The implant of claim 1, wherein the adjacent vertebral bodies are spaced apart at least in part further in the final deployed position than in the initial insertion position.

8. The implant of claim 1, wherein said upper and lower walls have at least one opening allowing for communication between said upper and lower walls, said opening being capable of containing fusion promoting materials for promoting bone ingrowth through said implant from the vertebral endplate of one of the adjacent vertebral bodies to the vertebral endplate of the other of said adjacent vertebral bodies for fusion of said adjacent vertebral bodies.

9. The implant of claim 1, wherein said first pair of diagonally opposed junctions are arcuate.

10. The implant of claim 9, wherein said arcuate junctions are arcs of radii.

11. The implant of claim 10, wherein said arcs of radii are each of the same radius.

12. The implant of claim 10, wherein said arcs of radii have a radius defining a portion of the same circle.

13. The implant of claim 10, wherein said arcs of radii comprise chords of a circle.

14. The implant of claim 13, wherein said arcs of radii comprise chords of the same circle.

15. The implant of claim 13, wherein said arcs of radii comprise quadrants of the same circle.

16. The implant of claim 13, wherein the distance between said arcs of radii generally approximates the height of said body.

17. The implant of claim 10, wherein the distance between said arcs of radii is slightly less than the height of said body.

18. The implant of claim 10, wherein the distance between said arcs of radii is slightly greater than the height of said body.

19. The implant of claim 16, wherein the h eight of said body is no greater than the width of said body, and said fins extend from said upper and lower walls a height sufficient to make the overall height of said implant, when in the final deployed position as measured across the fins, greater than the width of said body.

20. The implant of claim 16, wherein the height of said body is greater than the width of said body, and said fins extend from said upper and lower walls.

21. The implant of claim 1, wherein said first pair of diagonally opposed junctions are chamfered.

22. The implant of claim 1, wherein said second pair of diagonally opposed junctions are corners.

23. The implant of claim 22, wherein each of said corners form approximately a 90 degree angle.

24. The implant of claim 22, wherein each of said corners form an angle between 45 and 135 degrees.

25. The implant of claim 1, wherein said second pair of diagonally opposed junctions are chamfered.

26. The implant of claim 1, wherein said second pair of diagonally opposed junctions are radiused.

27. The implant of claim 1, wherein said fins have a height measured from the longitudinal central axis of said implant, said height being substantially uniform along a portion of the length of said implant.

28. The implant of claim 1, wherein said fins have a height measured from each of said upper and lower walls, 29. The implant of claim 1, wherein said fins have a sharp leading edge for penetrating the vertebral endplates upon rotation of said implant.

30. The implant of claim 1, wherein said fins are protrusions.

31. The implant of claim 1, wherein said fins are evenly spaced along at least a portion of said upper and lower walls.

32. The implant of claim 1, wherein said implant is configured to have a single direction of rotation such that in rotating said implant 45 degrees said first pair of diagonally opposed junctions has a diagonal substantially the same as the height of said body of said implant contacting the adjacent vertebral bodies prior to rotation.

33. The implant of claim 1, wherein said implant is configured to have a single direction of rotation such that in rotating said implant 45 degrees said first pair of diagonally opposed junctions has a diagonal slightly less than the width of said body of said implant contacting the adjacent vertebral bodies prior to rotation.

34. The implant of claim 1, wherein said implant is configured to have a single direction of rotation such that in rotating said implant 45 degrees said first pair of diagonally opposed junctions has a diagonal slightly greater than the width of said body of said implant contacting the adjacent vertebral bodies prior to rotation.

35. The implant of claim 1, wherein said body has a hollow portion.

36. The implant of claim 35, wherein said hollow portion is adapted to contain fusion promoting material.

37. The implant of claim 35, wherein said upper and lower walls have at least one opening passing therethrough in communication with said hollow portion.

38. The implant of claim 37, wherein said side walls have at least one opening passing therethrough in communication with said hollow portion.

39. The implant of claim 1, wherein said implant is capable of retaining fusion promoting material.

40. The implant of claim 35, wherein at least one of said leading end and said trailing end of said body has an opening in communication with said hollow portion and adapted to cooperatively engage a cap.

41. The implant of claim 40, further comprising a removable cap for closing said opening in at least one of said leading end and said trailing end of said body.

42. The implant of claim 37, wherein at least some of said openings have a maximum cross sectional dimension of approximately 0.5 mm to 5 mm.

43. The implant of claim 37, wherein at least some of said openings are greater than microscopic size.

44. The implant of claim 37, wherein said at least one opening includes a plurality of openings of which a portion are less than 15 microns across their largest dimension.

45. The implant of claim 37, wherein at least some of said openings pass through said upper and lower walls forming channels through said body.

46. The implant of claim 1, wherein said body has a plurality of openings passing therethrough adapted to allow bone to grow through said implant from one of the adjacent vertebral bodies to another of the adjacent vertebral bodies.

47. The implant of claim 1, wherein said implant is made of a material that is stronger than bone.

48. The implant of claim 1, wherein said implant is made of a material that is harder than bone.

49. The implant of claim 1, wherein said implant is made of a surgical grade implant material that is metallic.

50. The implant of claim 1, wherein at least a portion of said body is porous.

51. The implant of claim 1, wherein at least a portion of said body is treated to promote bone ingrowth between said implant and one of the vertebral bodies.

52. The implant of claim 1, for use in the lumbar spine wherein said body has a length in the range of 20–34 mm.

53. The implant of claim 52, wherein said side walls are spaced from one another in the range of 6–20 mm.

54. The implant of claim 52, wherein said upper and lower walls are spaced from one another in the range of 6–20 mm.

55. The implant of claim 52, wherein said fins have a height extending from said upper and lower walls in the range of 1–5 mm.

56. The implant of claim 1, wherein at least one of said ends includes an engagement portion for engaging an instrument for the insertion of said implant.

57. The implant of claim 1, wherein said implant comprises a material other than bone.

58. The implant of claim 1, wherein said implant comprises bone.

59. The implant of claim 58, wherein said bone includes cortical bone.

60. The implant of claim 58, wherein said implant comprises bone growth promoting material.

61. The implant of claim 60, wherein said bone growth promoting material is selected from one of bone morphogenetic protein, hydroxyapatite, and genes coding for the production of bone.

62. The implant of claim 1, wherein said implant is treated with a bone growth promoting substance.

63. The implant of claim 1, wherein said implant is at least in part bioabsorbable.

64. The implant of claim 1, wherein said implant comprises metal.

65. The implant of claim 64, wherein said metal is ASTM material suitable for use in said implant.

66. The implant of claim 64, wherein said implant includes titanium.

67. The implant of claim 1, wherein said implant comprises a plastic material.

68. The implant of claim 1, wherein said implant comprises a ceramic material.

69. The implant of claim 1, wherein said implant is formed of a material that intrinsically participates in the growth of bone from one of the adjacent vertebral bodies to the other of the adjacent vertebral bodies.

70. The implant of claim 1, wherein at least a portion of said implant is treated to promote bone ingrowth between said implant and said adjacent vertebral bodies.

71. An interbody spinal implant set for insertion across a disc space between adjacent vertebral bodies of a human spine, the implant set comprising:

a first implant comprising:

a body having an insertion end, a trailing end, opposed side walls, and upper and lower walls, said body having a cross-section with a height measured between said upper and lower walls and a width measured between said side walls, said side walls intersecting said upper and lower walls at four junctions, a first pair of diagonally opposed junctions having a distance therebetween substantially the same as the height of said body, a second pair of diagonally opposed junctions having a distance therebetween greater than the distance of said first pair of diagonally opposed junctions; and fins extending outwardly from said opposed upper and lower walls adapted to penetrate the vertebral endplates of the adjacent vertebral bodies upon rotation of the implant in a first direction substantially 90 degrees from an initial insertion position to a final deployed position; and a second implant comprising:

a body having an insertion end, a trailing end, opposed side walls, and upper and lower walls, said body having a cross-section with a height measured between said upper and lower walls and a width measured between said side walls, said side walls intersecting said upper and lower walls at four junctions, a first pair of diagonally opposed junctions having a distance therebetween less than the height of said body, a second pair of diagonally opposed junctions having a distance therebetween greater than the distance between said first pair of diagonally opposed junctions; and fins extending outwardly from said opposed upper and lower walls adapted to penetrate the vertebral endplates of the adjacent vertebral bodies upon rotation of the implant in a second direction opposite said first direction and substantially 90 degrees from an initial insertion position to a final deployed position.

72. The implant set of claim 71, further comprising a third implant for placement between said first and second implants, said third implant having contacting surfaces for contacting one of said opposed side walls of each of said first and second implants.

73. The implant set of claim 72, wherein said contacting surfaces of said third implant interconnect with said first and second implants.

74. The implant set of claim 72, wherein said contacting surfaces of said third implant include ridges facing opposite the direction of insertion for inhibiting said third implant from expulsion once inserted between said adjacent vertebral bodies.

75. The implant set of claim 74, wherein said side wall of each of said first and second implants facing toward said third implant includes ridges cooperatively oriented for interlocking with said ridges of said third implant.

76. The implant set of claim 71, wherein said side walls of each of said first and second implants have a distance therebetween adapted to contact the adjacent vertebral bodies upon initial insertion of said implant into the spine.

77. The implant set of claim 71, wherein each of said side walls of said first and second implants are planar.

78. The implant set of claim 77, wherein said side walls of each of said first and second implants are generally parallel to one another.

79. The implant set of claim 71, wherein said upper and lower walls of each of said first and second implants have a distance therebetween adapted to support the vertebral endplates of the adjacent vertebral bodies upon rotation of said implant from an initial insertion position to a deployed position in the disc space.

80. The implant set of claim 71, wherein said upper and lower walls of each of said first and second implants have at least one opening allowing for communication between said upper and lower walls, said opening being capable of containing fusion promoting materials for promoting bone ingrowth through said implant from the vertebral endplate of one of the adjacent vertebral bodies to the vertebral endplate of the other of said adjacent vertebral bodies for fusion of the adjacent vertebral bodies.

81. The implant set of claim 71, wherein said first pair of diagonally. opposed junctions of each of said first and second implants are arcs of radii.

82. The implant set of claim 81, wherein the distance between said arcs of radii of each of said first and second implants generally approximates the height of said body.

83. The implant set of claim 81, wherein the distance between said arcs of radii of each of said first and second implants is slightly less than the height of said body.

84. The implant set of claim 81, wherein the distance between said arcs of radii of each of said first and second implants is slightly greater than the height of said body.

85. The implant set of claim 71, wherein the height of said body of said first and second implants is no greater than the width of said body of said first and second implants, respectively, and said fins extend from said upper and lower walls of each of said first and second implants a height sufficient to make the overall height of said first and second implants, when in the final deployed position as measured across the fins, greater than the width of said body.

86. The implant set of claim 71, wherein the height of said body of said first and second implants is greater than the width of said body of said first and second implants, respectively, and said fins extend from said upper and lower walls of each of said first and second implants a height sufficient to make the overall height of said first and second implants, when in the final deployed position as measured across the fins, greater than the width of said body.

87. The implant set of claim 71, wherein said first pair of diagonally opposed junctions of at least one of said first and second implants are chamfered.

88. The implant set of claim 71, wherein said second pair of diagonally opposed junctions of at least one of said first and second implants are corners.

89. The implant set of claim 71, wherein said second pair of diagonally opposed junctions of at least one of said first and second implants are chamfered.

90. The implant set of claim 71, wherein said second pair of diagonally opposed junctions of at least one of said first and second implants are radiused.

91. The implant set of claim 71, wherein said fins of said first and second implants have a sharp leading edge for penetrating the vertebral endplates upon rotation of said implant.

92. The implant set of claim 71, wherein said fins of said first and second implants are protrusions.

93. The implant set of claim 71, wherein each of said first and second implants are configured to have a single direction of rotation such that in rotating each of said implants 45 degrees said first pair of diagonally opposed junctions of each of said first and second implants has a diagonal substantially the same as the width of said body of said first and second implants, respectively, contacting the adjacent vertebral bodies prior to rotation.

94. The implant set of claim 71, wherein each of said first and second implants are configured to have a single direction of rotation such that in rotating each of said implants 45 degrees said first pair of diagonally opposed junctions of each of said first and second implants has a diagonal slightly less than the width of said body of said first and second implants, respectively, contacting the adjacent vertebral bodies prior to rotation.

95. The implant set of claim 71, wherein each of said first and second implants are configured to have a single direction of rotation such that in rotating each of said implants 45 degrees said first pair of diagonally opposed junctions of each of said first and second implants has a diagonal slightly greater than the width of said body of said first and second implant, respectively, contacting the adjacent vertebral bodies prior to rotation.

96. The implant set of claim 71, wherein said body of at least one of said first and second implants has a hollow portion.

97. The implant set of claim 96, wherein said hollow portion of said at least one of said first and second implants is adapted to contain fusion promoting material.

98. The implant set of claim 96, wherein said upper and lower walls of at least one of said first and second implants have at least one opening passing therethrough in communication with said hollow portion.

99. The implant set of claim 71, wherein at least one of said first and second implants is capable of retaining fusion promoting material.

100. The implant set of claim 96, wherein at least one of said leading end and said trailing end of said body of at least one of said first and second implants has an opening in communication with said hollow portion and adapted to cooperatively engage a cap.

101. The implant set of claim 100, further comprising a removable cap for closing said opening in at least one of said leading end and said trailing end of said body of at least one of said first and second implants.

102. The implant set of claim 71, wherein at least one of said first and second implants is made of a surgical grade implant material that is metallic.

103. The implant set of claim 71, wherein at least a portion of said body of at least one of said first and second implants is porous.

104. The implant set of claim 71, wherein at least a portion of said body of at least one of said first and second implants is treated to promote bone ingrowth between said at least one implant and one of said vertebra.

105. The implant set of claim 71, wherein at least one of said ends of said first and second implants includes an engagement portion for engaging an instrument for the insertion of said first and second implant.

* * * * *

UNITED STATES PATENT AND TRADEMARK OFFICE
CERTIFICATE OF CORRECTION

PATENT NO.  : 6,537,320 B1  
DATED       : March 25, 2003  
INVENTOR(S) : Gary K. Michelson, M.D.

Page 1 of 2

It is certified that error appears in the above-identified patent and that said Letters Patent is hereby corrected as shown below:

<u>Title page,</u>
Item [74], Under *Attorney, Agent, or Firm*, change "LI" to -- LLP --;

<u>Column 20,</u>
Line 32, change "13" to -- 10 --;
Line 40, change "h eight" to -- height --;

<u>Column 23,</u>
Line 66, change "diagonally." to -- diagonally --; and

<u>Column 26,</u>
Insert after line 16,
-- 106. The implant of claim 1, wherein said upper and lower walls are disposed at least in part in a diverging angular relationship to each other from said insertion end to said trailing end of said body.

107. The implant of claim 1, wherein said upper and lower walls are disposed at least in part in a converging angular relationship to each other from said insertion end to said trailing end of said body.

108. The implant of claim 1, wherein said upper and lower walls have a generally anatomical shape configured to substantially match the natural contours of that portion of the endplates of the two adjacent vertebral bodies to be fused to which said walls are applied.

109. The implant of claim 1, wherein said fins have a height measured from the longitudinal central axis of said implant, said height being variable along the length of said implant.

110. The implant of claim 1, wherein said fins have a height measured from each of said upper and lower walls, respectively, said height being varied along the length of said implant.

111. The implant of claim 1, in combination with an osteogenic material.

112. The implant of claim 111, wherein said osteogenic material includes at least one of harvested bone, bone morphogenetic protein, hydroxapatite, hydroxyapatite tricalcium phosphate, and genes coding for the production of bone.

UNITED STATES PATENT AND TRADEMARK OFFICE
CERTIFICATE OF CORRECTION

PATENT NO.    : 6,537,320 B1
DATED         : March 25, 2003
INVENTOR(S)   : Gary K. Michelson, M.D.

It is certified that error appears in the above-identified patent and that said Letters Patent is hereby corrected as shown below:

<u>Column 26, (cont'd)</u>

113. The implant set of claim 71, wherein said upper and lower walls of each of said first and second implants are disposed at least in part in a diverging angular relationship to each other from said insertion end to said trailing end of said body.

114. The implant set of claim 71, wherein said upper and lower walls of each of said first and second implants are disposed at least in part in a converging angular relationship to each other from said insertion end to said trailing end of said body.

115. The implant set of claim 71, wherein said upper and lower walls of each of said first and second implants have a generally anatomical shape configured to substantially match the natural contours of that portion of the endplates of the two adjacent vertebral bodies to be fused to which said walls are applied.

116. The implant of claim 71, in combination with an osteogenic material.

117. The implant of claim 116, wherein said osteogenic material includes at least one of harvested bone, bone morphogenetic protein, hydroxyapatite, hydroxyapatite tricalcium phosphate, and genes coding for the production of bone. --.

Signed and Sealed this

Seventeenth Day of June, 2003

JAMES E. ROGAN
*Director of the United States Patent and Trademark Office*